(12) United States Patent
Chen et al.

(10) Patent No.: US 7,084,270 B2
(45) Date of Patent: Aug. 1, 2006

(54) PYRIMIDO COMPOUNDS HAVING ANTIPROLIFERATIVE ACTIVITY

(75) Inventors: Yi Chen, Nutley, NJ (US); Andrzej Robert Daniewski, Clifton, NJ (US); William Harris, Henlow (GB); Marek Michal Kabat, Nutley, NJ (US); Emily Aijun Liu, Nutley, NJ (US); Jin-Jun Liu, Warren, NJ (US); Kin-Chun Luk, North Caldwell, NJ (US); Christophe Michoud, New York, NY (US)

(73) Assignee: Hoffman-La Roche Inc., Nutley, NJ (US)

( * ) Notice: Subject to any disclaimer, the term of this patent is extended or adjusted under 35 U.S.C. 154(b) by 425 days.

(21) Appl. No.: 10/623,972

(22) Filed: Jul. 21, 2003

(65) Prior Publication Data

US 2004/0038995 A1 Feb. 26, 2004

Related U.S. Application Data

(60) Provisional application No. 60/403,519, filed on Aug. 14, 2002.

(51) Int. Cl.
*C07D 487/04* (2006.01)
*C07D 25/00* (2006.01)
*A01N 43/90* (2006.01)
*A61K 31/519* (2006.01)

(52) U.S. Cl. .................................. 544/256; 514/262.1
(58) Field of Classification Search ................. 544/256; 514/262.1
See application file for complete search history.

(56) References Cited

U.S. PATENT DOCUMENTS

| | | | |
|---|---|---|---|
| 2,949,466 | A | 8/1960 | Hoefle et al. |
| 3,939,084 | A | 2/1976 | Sullivan |
| 4,425,346 | A | 1/1984 | Horlington |
| 4,886,807 | A | 12/1989 | Kitamura et al. |
| 6,150,373 | A | 11/2000 | Harris et al. |
| 6,451,804 | B1 | 9/2002 | Dunn et al. |
| 2004/0019210 | A1 | 1/2004 | Connolly et al. |

FOREIGN PATENT DOCUMENTS

| | | |
|---|---|---|
| WO | WO 98/24432 | 6/1998 |
| WO | WO 99/61444 | 12/1999 |
| WO | WO 00/24744 | 5/2000 |
| WO | WO 01/29041 | 4/2001 |
| WO | WO 01/29041 A1 | 4/2001 |
| WO | WO 01/29042 | 4/2001 |
| WO | WO 01/64679 A1 | 9/2001 |
| WO | WO 02/18380 A1 | 3/2002 |

OTHER PUBLICATIONS

Hennequin, L. F. et al., *J. Med. Chem.* 2002, vol. 45(6) pp. 1300–1312.
Klohs W. E. et al., *Current Opinion in Biotechnology 1999*, vol. 10, pp. 544–549.
Ansel, H. et al., *Pharmaceutical Dosage Forms & Drug Delivery Systems* 6th Ed. 1995, p. 196.
J. Alexander, et al., *J. Med. Chem. 1988*, vol. 31, pp. 318–322.
Masquelin et al., *Helvetica Chimica Acta*, vol. 81 (1998) pp. 646–659.
Devi, et al., *Indian Journal of Heterocyclic Chemistry*, vol. 7, Jan.—Mar., 1998, pp. 193–196.
Tominaga et al., *Chemical & Pharmaceutical Bulletin*, vol. 32, No. 1, Jan. 1984, pp. 122–129.
Tominaga et al., *Hetercycles*, vol. 12, No. 4, 1979, pp. 503–504.
Marsh et al., *Chemical Communications*, 1996, pp. 1527–1528.
Z. Chem. 20 Jg (1980) Heft. 11, pp. 412–413.
Cappuccino et al., *Cancer Research*, vol. 24, Aug. 1964, pp. 1243–1248.
Chatterjee et al., *J. Sci. Industr. Res.*, vol. 17B, Feb., 1958, pp. 63–70.
Chatterjee et al., *J. Sci. Industr. Res.*, vol. 18B, Jul., 1959, pp. 272–278.
Graboyes et al., *Pteridines X.*, vol. 11 Jan. 6, 1968, pp. 568–573.
Grohe et al., *Liebigs Ann. Chem.*, 1974, pp. 2066–2073.
Gulevskaya et al., *Chemistry of Heterocyclic Compounds*, vol. 30, No. 9, 1994, pp. 1083–1091.
Hirota et al., *J. Chem. Soc. Perkin Trans. I*, 1990, pp. 123–128.
Srivastava, et al., *Combinatorial Chemistry & High Throughput Screening*, 1999, 2, pp. 33–37.
Taylor et al., *Pyrimido [4,5-D]Pyrimidines*, vol. 82, pp. 5711–5718, no date available.
Wamhoff et al., *Heterocycles*, vol. 35, No. 2, 1993, pp. 1055–1066.
M. Hirota et al., "A Facile Synthesis of 7–Substituted Pyrimido[4,5–d]–Pyrimidine–2,4–diones", *Synthesis*, pp. 589–590 (1984).

*Primary Examiner*—James O. Wilson
*Assistant Examiner*—Paul V. Ward
(74) *Attorney, Agent, or Firm*—George W. Johnston; Patricia S. Rocha-Tramaloni

(57) ABSTRACT

Disclosed are novel pyrimido compounds that are selective inhibitors of both KDR an FGFR kinases and are selective against LCK. These compounds and their pharmaceutically acceptable salts are anti-proliferative agents useful in the treatment or control of solid tumors, in particular breast, colon, lung and prostate tumors. Also disclosed are pharmaceutical compositions containing these compounds and methods of treating cancer.

17 Claims, No Drawings

PYRIMIDO COMPOUNDS HAVING ANTIPROLIFERATIVE ACTIVITY

CONTINUITY INFORMATION

This application claims priority of Provisional application Ser. No. 60/403,519, filed Aug. 14, 2002.

FIELD OF THE INVENTION

The present invention is directed to novel pyrimido compounds of formula

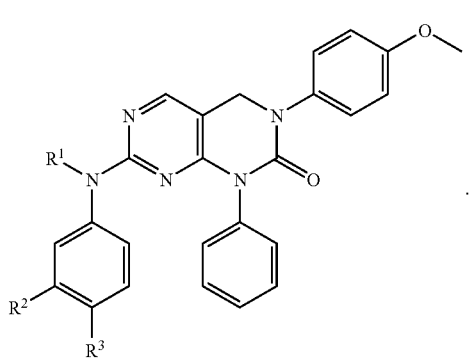

I

These compounds inhibit KDR (kinase insert domain-containing receptor) and FGFR (fibroblast growth factor receptor) kinases and are selective against LCK (T-cell tyrosine kinase p56$^{lck}$). These compounds and their pharmaceutically acceptable salts have antiproliferative activity and are useful in the treatment or control of cancer, in particular solid tumors. In addition these compounds have advantageous bioavailability profiles. This invention is also directed to pharmaceutical compositions containing such compounds and to methods of treating or controlling cancer, most particularly the treatment or control of breast, lung, colon and prostate tumors.

BACKGROUND OF THE INVENTION

Protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

Tyrosine kinases are a subset of protein kinases that catalyze the transfer of the terminal phosphate of adenosine triphosphate to tyrosine residues on protein substrates. These kinases play an important part in the propagation of growth factor signal transduction that leads to cellular proliferation, differentiation and migration.

For example, fibroblast growth factor (FGF) and vascular endothelial growth factor (VEGF) have been recognized as important mediators of tumor promoted angiogenesis. VEGF activates endothelial cells by signaling through two high affinity receptors, one of which is the kinase insert domain-containing receptor (KDR). See Hennequin L. F. et. al., J. Med. Chem. 2002, 45(6), pp 1300. FGF activates endothelial cells by signaling through the FGF receptor (FGFR). Solid tumors depend upon the formation of new blood vessels (angiogenesis) to grow. Accordingly, inhibitors of the receptors FGFR and KDR that interfere with the growth signal transduction, and thus slow down or prevent agiogenisis, are useful agents in the prevention and treatment of solid tumors. See Klohs W. E. et. al., Current Opinion in Biotechnology 1999, 10, p. 544.

There are several examples of small molecule inhibitors of protein kinase catalytic activity. In particular, small molecule inhibitors typically block the phosphorylation of substrates by tightly interacting with the protein kinase ATP binding site (or "active site"). See WO 98/24432 and Hennequin L. F. et. al., J. Med. Chem. 2002, 45(6), pp 1300. Several of these compounds inhibit multiple targets. For example, WO99/61444 (Warner-Lambert) discloses bicyclic pyrimidines and bicyclic 3,4-dihydropyrimidines of formula

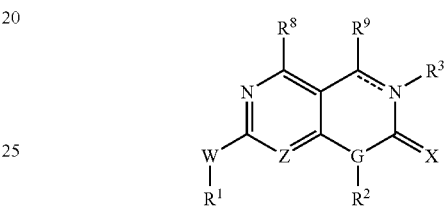

that are asserted to inhibit cyclin dependent kinases Cdk1, Cdk2 and Cdk4 as well as the growth factor receptor tyrosine kinase enzymes PDGFR and FGFR. Some compounds are also asserted to inhibit Cdk6.

U.S. Pat. No. 6,150,373 (Hoffmann-LaRoche Inc.) discloses bicyclic nitrogen heterocycles of formula

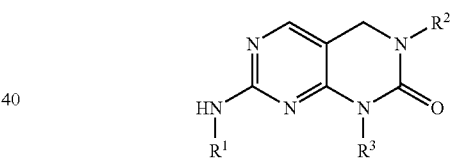

that are stated to inhibit the T-cell tyrosine kinase p56$^{lck}$.

There continues to be a need for easily synthesized, small-molecule compounds effective in inhibiting the catalytic activity of protein kinases, in particular FGF and KDR kinases for treating one or more types of solid tumors. It is particularly desirable to provide small molecule inhibitors that are selective for FGF and KDR. This is desirable because of the potential concomitant toxicity and other undesirable complications that may follow from inhibiting multiple targets. It is preferable that such small molecule inhibitors also possess advantageous bioavailability profiles. It is thus an object of this invention to provide such compounds and pharmaceutical compositions containing these compounds.

SUMMARY OF THE INVENTION

The present invention is directed to novel pyrimido compounds capable of selectively inhibiting the activity of KDR and FGFR. These compounds are useful in the treatment or control of cancer, in particular the treatment or control of solid tumors. In particular this invention is directed to a compound of formula

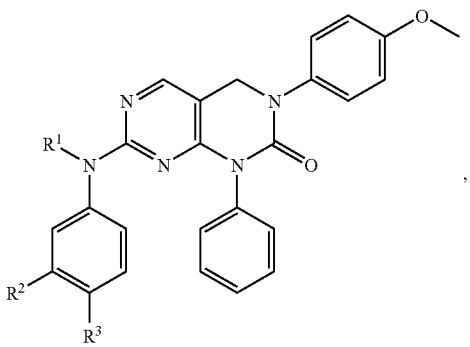

or the pharmaceutically acceptable salts thereof, wherein
$R^1$ is selected from the group
—H,
—$COR^4$, and
—$COOCHR^5OCOR^4$;
$R^2$ and $R^3$ are independently selected from
—H, and
—$OR^5$;
$R^4$ is selected from the group
—$C_{1-6}$ alkyl,
-lower alkyl substituted by up to 4 groups independently selected from
—$NR^5R^6$,
—$SR^5$,
—$OR^5$,
-aryl,
-aryl substituted by up to 2 groups independently selected from —$OR^5$ and $C_{1-4}$ lower alkyl, and
-heteroaryl, and
-heterocycle;
$R^5$ and $R^6$ are independently selected from
—H
$C_{1-5}$ lower alkyl, or
alternatively, —$NR^5R^6$ can form a ring having 3 to 7 atoms, said ring optionally including one or more additional N or O atoms.

The present invention is also directed to pharmaceutical compositions comprising a therapeutically effective amount of one or more compounds of formula I and a pharmaceutically acceptable carrier or excipient.

The present invention is further directed to a method for treating solid tumor, in particular breast or colon tumors, by administering to a human patient in need of such therapy an effective amount of a compound of formula I and/or its salt.

The present invention is further directed to novel intermidate compounds useful in the preparation of compounds of formula I.

DETAILED DESCRIPTION OF THE INVENTION

Definitions

As used herein, the following terms shall have the following definitions.

"Aryl" means an aromatic carbocyclic radical, for example a 6–10 membered aromatic or partially aromatic ring system. Preferred aryl groups include, but are not limited to, phenyl, naphthyl, tolyl and xylyl.

"Cycloalkyl" means a non-aromatic, partially or completely saturated cyclic aliphatic hydrocarbon group containing 3 to 8 atoms. Examples of cycloalkyl groups include cyclopropyl, cyclopentyl and cyclohexyl.

"Effective amount" means an amount that is effective to prevent, alleviate or ameliorate symptoms of disease or prolong the survival of the subject being treated.

"Halogen" means fluorine, chlorine, bromine or iodine, preferably chlorine

"Hetero atom" means an atom selected from N, O and S, preferably N.

"Heteroaryl" means an aromatic heterocyclic ring system containing up to two rings. Preferred heteroaryl groups include, but are not limited to, thienyl, furyl, indolyl, pyrrolyl, pyridinyl, pyridine, pyrazinyl, oxazolyl, thiaxolyl, quinolinyl, pyrimidinyl, imidazole and tetrazolyl.

"Heterocycle" or "heterocyclyl" means a saturated or partially unsaturated aromatic monovalent cyclic radical have from one to 3 hetero atoms selcted from nitrogen, oxygen or sulfur or a combination thereof. Examples of preferred heterocycles are peperidine, peperazine, pyrrolidine, and morpholine.

"$IC_{50}$" refers to the concentration of a particular compound according to the invention required to inhibit 50% of a specific measured activity. $IC_{50}$ can be measured, inter alia, as is described in Example 22, infra.

"Lower Alkyl" denotes a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl and hexyl. As used herein the sample designation $C_{1-4}$ lower alkyl means alkyl having from 1 to 4 carbon atoms.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to which the particular compound is administered.

"Substituted," as in substituted alkyl, means that the substitution can occur at one or more positions and, unless otherwise indicated, that the substituents at each substitution site are independently selected from the specified options.

"Therapeutically effective amount" means an amount of at least one compound of Formula I, or a pharmaceutically acceptable salt or ester thereof, that significantly inhibits proliferation and/or prevents differentiation of a human tumor cell, including human tumor cell lines.

PREFERRED EMBODIMENTS

In one embodiment the invention is directed to a compound of formula:

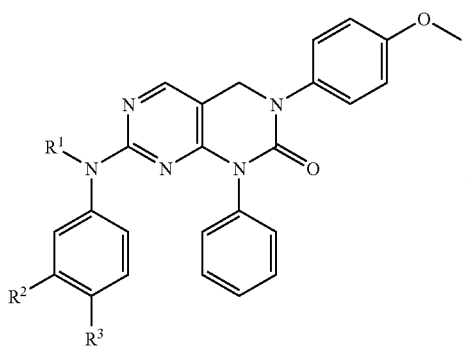

or the pharmaceutically acceptable salts thereof, wherein
$R^1$ is selected from the group
—H,
—COR$^4$, and
—COOCHR$^5$OCOR$^4$;
$R^2$ and $R^3$ are independently selected from
—H, and
—OR$^5$;
$R^4$ is selected from the group
—C$_{1-6}$ alkyl,
-lower alkyl substituted by up to 4 groups independently selected from
—NR$^5$R$^6$,
—SR$^5$,
—OR$^5$,
-aryl,
-aryl substituted by up to 2 groups independently selected from —OR$^5$ and C$_{1-4}$ lower alkyl, and
-heteroaryl, and
-heterocycle;
$R^5$ and $R^6$ are independently selected from
—H
C$_{1-5}$ lower alkyl, or
alternatively, —NR$^5$R$^6$ can form a ring having 3 to 7 atoms, said ring optionally including one or more additional N or O atoms.

In a preferred embodiment, the invention is directed to a compound of formula I wherein $R^1$ is —COR$^4$.

In another preferred embodiment, the invention is directed to a compound of formula I wherein $R^1$ is —COOCHR$^5$OCOR$^4$.

In another preferred embodiment of the compounds of formula I, $R^2$ is H.

In another preferred embodiment of the compounds of formula I, $R^2$ and $R^3$ are H.

The following compounds are preferred embodiments according to the present invention:

3-(4-Methoxyphenyl)-1-phenyl-7-(phenylamino)-1,3,4-trihydropyrimidino[4,5-d]pyrimidin-2-one, 3-(4-Methoxyphenyl)-1-phenyl-7-(phenylamino)-1,3,4-trihydropyrimidino[4,5-d]pyrimidin-2-one methanesulfonate salt, 7-[(4-Hydroxyphenyl)amino]-3-(4-methoxyphenyl)-1-phenyl-1,3,4-trihydropyrimidino[4,5-d]pyrimidin-2-one, 3-(4-Methoxyphenyl)-7-[(4-methoxyphenyl)amino]-1-phenyl-1,3,4-trihydropyrimidino[4,5-d]pyrimidin2-one, N-[3-(4-Methoxyphenyl)-2-oxo-1-phenyl(1,3,4-trihydropyrimidino[4,5-d]pyrimidin-7-yl)]-N-phenylacetamide, N-[3-(4-methoxyphenyl)-2-oxo-1-phenyl(1,3,4-trihydropyrimidino[4,5-d]pyrimidin-7-yl)]-N-phenylpropanamide, {N-[3-(4-Methoxyphenyl)-2-oxo-1-phenyl(1,3,4-trihydropyrimidino[4,5-d]pyrimidin-7-yl)]-N-phenylcarbamoyloxy}methyl acetate, N-[3-(4-Methoxyphenyl)-2-oxo-1-phenyl(1,3,4-trihydropyrimidino[4,5-d]pyrimidin-7-yl)]-N-phenylpentanamide, N-[3-(4-Methoxyphenyl)-2-oxo-1-phenyl(1,3,4-trihydropyrimidino[4,5-d]pyrimidin-7-yl)]-N-phenylbutanamide, N-(4-Hydroxyphenyl)-N-[3-(4-methoxyphenyl)-2-oxo-1-phenyl(1,3,4-trihydropyrimidino[4,5-d]pyrimidin-7-]acetamide, and N-(4-methoxyphenyl)-N-[3-(4-methoxyphenyl)-2-oxo-1-phenyl(1,3,4-trihydropyrimidino[4,5-d]pyrimidin-7-]acetamide, The compounds of the invention are selective for FGF and KDR kinases. These compounds are useful in the treatment or control of cancer, in particular the treatment or control of solid tumors, specifically breast, lung, colon and prostate tumors. These compounds are soluble and thus possess advantageous bioavailability profiles such as improved oral bioavailability.

General Synthesis of Compounds According to the Invention

The compounds of the present invention can be prepared by any conventional means. Suitable processes for synthesizing these compounds are provided in the examples. Generally, compounds of formula I can be prepared according to the below described synthetic route.

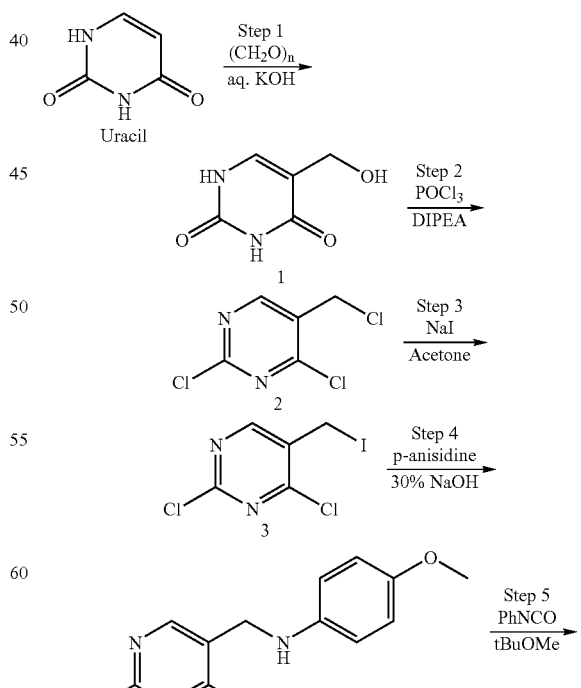

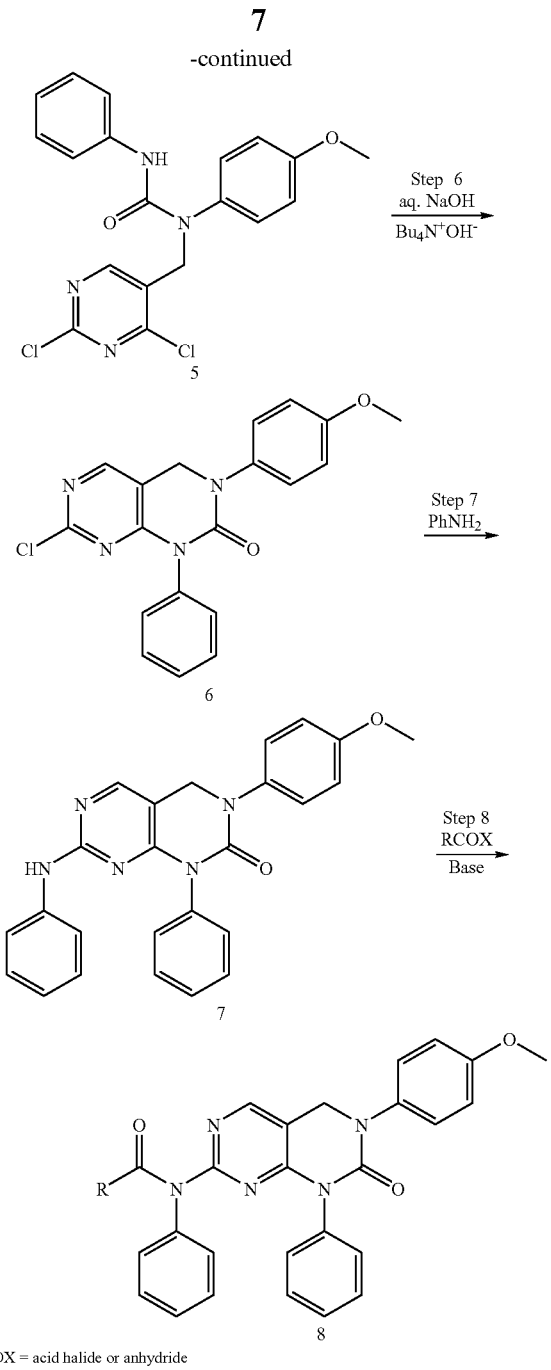

RCOX = acid halide or anhydride

Synthesis of compounds of formula I where $R^1$=—COOCHR$^5$OCOR$^4$ is well known in the art and is documented in J. Alexander, R. Cargill, S. R. Michelson, H. Schwam *J. Med. Chem.* 1988, 31, 318–322.

Compositions/Formulations

In an alternative embodiment, the present invention is directed to pharmaceutical compositions comprising at least one compound of formula I, or a pharmaceutically acceptable salt or ester thereof.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the salts thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of the present invention, including the compounds of formula I, are useful in the treatment or control of cell proliferative disorders, in particular oncological disorders. These compounds and formulations containing said compounds are particularly useful in the treatment or control of solid tumors, such as, for example, breast, colon, lung and prostate tumors. Thus, the present invention is further directed to a method for treating such solid tumors by administering to a patient in need of such therapy an effective amount of a compound of formula I and/or its salt.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

The present invention is also directed to the following novel intermediates useful in the synthesis of compounds of formula I:

(Chloromethoxy)-N-[3-(4-methoxyphenyl)-2-oxo-1-phenyl(1,3,4-trihydropyrimidino[4,5-d]pyrimidin-7-yl)]-N-benzamide [Example 4a]

3-(4-Methoxyphenyl)-1-phenyl-7-{[4-(1,1,2,2-tetramethyl-1-silapropoxy) phenyl]amino}-1,3,4-trihydropyrimidino[4,5-d]pyrimidin-2-one [Example 19c], and N-[3-(4-Methoxyphenyl)-2-oxo-1-phenyl(1,3,4-trihydropyrimidino[4,5-d]pyrimidin-7-yl)]-N-[4-(1,1,2,2-tetramethyl-1-silapropoxy)phenyl]acetamide [Example 19d].

EXAMPLES

The following examples illustrate preferred methods for synthesizing the compounds and formulations of the present invention.

Example 1

Example 1a 5-(Hydroxymethyl)-1,3-dihydropyrimidine-2,4-dione

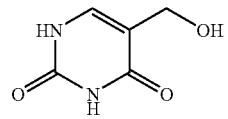

A 2-L, three-necked flask equipped with a mechanical stirrer, thermometer, condenser, and nitrogen-inlet bubbler was charged with uracil (185.0 g, 1650 mmol) (Aldrich), paraformaldehyde (61.50 g, 2050 mmol as formaldehyde) (Aldrich), and a solution of potassium hydroxide (86.9%, 59.95 g, 928.5 mmol) (Aldrich) in water (1.445 L). The mixture was stirred at 50–52° C. for 68 h. TLC analysis indicated complete reaction. After concentration at 60° C./14 mmHg to a volume of ca. 500 mL, the residue was diluted with acetone (500 mL). The resulting precipitate was collected by filtration, washed with acetone, and dried by suction, then at 50° C./25 mmHg to give crude 5-(hydroxymethyl)-1,3-dihydropyrimidine-2,4-dione (250 g) as a white solid. The combined mother liquor and washes were concentrated to a volume of ca. 100 mL and a solution of hydroxylamine hydrochloride (27.52 g, 396.0 mmol, Aldrich) in water (100 mL) was added. The resulting precipitate was collected by filtration, washed with acetone, and dried by suction to give second crop of crude 5-(hydroxymethyl)-1,3-dihydropyrimidine-2,4-dione (34 g) as a white solid. The two lots were combined (244 g, 4% overweight) and used directly in the next step.

Example 1b 2,4-Dichloro-5-(chloromethyl)pyrimidine

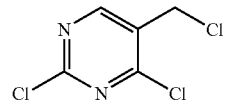

A 1-L, three-necked flask equipped with a mechanical stirrer, addition funnel, thermometer and nitrogen-inlet bubbler was charged with crude 5-(hydroxymethyl)-1,3-dihydropyrimidine-2,4-dione (50.25 g, ca. 340 mmol) (from Example 1a supra), phosphorous oxychloride (164.8 mL, 1768 mmol) (Aldrich), and toluene (100 mL). To this mixture was added N,N-diisopropylethylamine (184.7 mL, 1060 mmol) (Aldrich) over 10 min, while maintaining the temperature of the mixture below 70° C. using a water bath. After completion of the addition, the cooling bath was removed and the mixture was heated to reflux (113–116° C.) for 1 hour. Some of the toluene (ca. 35 mL) was removed by distillation to increase the temperature of the reaction mixture to 120° C. and the mixture was stirred at 120–123° C. for 5 hours. TLC analysis indicated reaction was complete. After the mixture was allowed to cool to room temperature overnight, the mixture was cautiously added, over 67 minutes, to a stirred bi-phasic mixture of water (200 mL) and isopropyl acetate (150 mL), while maintaining the temperature between 17° C. to 21° C. using an ice-water bath. After stirring at 18–21° C. for 80 minutes with occasional ice-water cooling, the mixture was extracted with toluene (4×150 mL). The combined organic layers were dried (sodium sulfate), filtered, then concentrated to dryness under reduced pressure to give of crude 2,4-dichloro-5-(chloromethyl)pyrimidine as a white solid, containing polar impurities. (Yield 56.1 g, 83.6% yield from uracil).

Crude 2,4-dichloro-5-(chloromethyl)pyrimidine (70.39 g) was dissolved in dichloromethane (80 mL) and the resulting solution was filtered through a pad of TLC grade silica gel (100 g). The silica gel was then washed with dichloromethane:hexanes (1 L, 7:3), and the combined filtrate and washes were concentrated to dryness under reduced pressure to give 2,4-dichloro-5-(chloromethyl)pyrimidine as a white solid. (Yield 58.77 g, 83.5% recovery, 69.8% overall yield from uracil). This compound is highly caustic.

Example 1c 2,4-Dichloro-5-(iodomethyl)pyrimidine

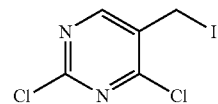

A 500-mL, round-bottom flask equipped with a magnetic stirrer, condenser, and nitrogen-inlet bubbler was charged with sodium iodide (38.5 g, 256.9 mmol) (Aldrich) and acetone (300 mL). After a clear solution was obtained, 2,4-dichloro-5-(chloromethyl)pyrimidine (50.0 g, 253.2 mmol) (from Example 1b supra) was added in one portion. After stirring at room temperature for 20 minutes, the mixture was heated to reflux for 15 minutes. NMR analysis indicated 98% conversion. After cooling to room temperature, the resulting precipitate (sodium chloride) was removed by filtration through a medium-sintered glass funnel and washed with acetone. The combined filtrate and washes were concentrated to a weight of ca. 75 g. The resulting concentrated solution of 2,4-dichloro-5-(iodomethyl)pyrimidine in acetone was diluted with toluene (20 mL). After concentration to a weight of ca.85 g in order to remove the residual acetone, this concentrated solution of 2,4-dichloro-5-(iodomethyl)pyrimidine in toluene was used directly in the next step.

Example 1d

[(2,4-Dichloropyrimidin-5-yl)methyl](4-methoxyphenyl)amine

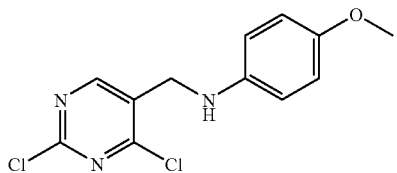

A 500-mL, three-necked flask equipped with a magnetic stirrer, thermometer, and nitrogen-inlet bubbler was charged with a solution of 2,4-dichloro-5-(iodomethyl)pyrimidine (85 g, ca. 253.2 mmol) (from Example 1c supra) in toluene (13.7 mL) from the previous step and toluene (96.3 mL, thus, a total of ca. 110 mL of toluene). After cooling with an ice-water bath, panisidine (31.18 g, 253.2 mmol) (Aldrich) was added. After stirring for 30 minutes, a solution of sodium hydroxide (13.54 g, 331.7 mmol) in water (50 mL) was added dropwise over 8 minutes, while maintaining the temperature of the reaction mixture at 10–15° C. Hexanes (55 mL) were added and the mixture was stirred at 10–15° C. for 45 minutes, then at room temperature for 22 hours to give a slurry. TLC analysis of the supernatant indicated complete reaction. The slurry was diluted with water (100 mL) and the solid was collected by filtration, washed with cold water and cold (−50° C.) methanol (100 mL), and dried by suction to give [(2,4-dichloropyrimidin-5-yl)methyl](4-methoxyphenyl)amine as an off-white solid; 97% pure by HPLC analysis. (Yield 59.87 g, 83.2%).

Example 1

N-[(2,4-Dichloropyrimidin-5-yl)methyl]-N-(4-methoxyphenyl)(phenylamino)carboxamide

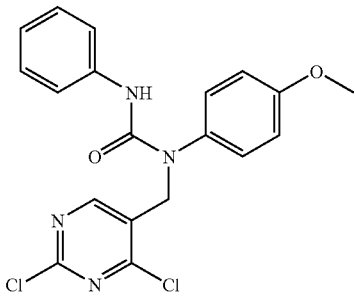

A 500-mL, three-necked flask equipped with a mechanical stirrer, thermometer, condenser, and nitrogen-inlet bubbler was charged with [(2,4-dichloropyrimidin-5-yl)methyl](4-methoxyphenyl)amine (59.6 g, 209.7 mmol) (from Example 1d supra) and tert-butyl methyl ether (300 mL) (Aldrich). After heating to 55° C. to give a clear solution, phenyl isocyanate (27.48 g, 230.7 mmol) (Aldrich) was added and the mixture was heated to reflux for 10 hours. TLC analysis indicated essentially complete reaction. After cooling to room temperature, the resulting solid was collected by filtration, washed with tert-butyl methyl ether (100 mL), and dried by suction to give N-[(2,4-dichloropyrimidin-5-yl)methyl]-N-(4-methoxyphenyl)(phenylamino) carboxamide as white crystals; 98.46% pure by HPLC analysis. (Yield 78.8 g, 91.3%).

Example 1f

7-Chloro-3-(4-methoxyphenyl)-1-phenyl-1,3,4-trihydropyrimidino[4,5-d]pyrimidin-2-one

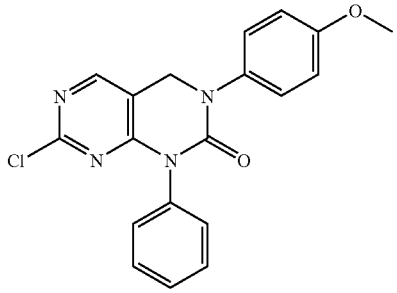

A 500-mL, three-necked flask equipped with a magnetic stirrer, thermometer, and nitrogen-inlet bubbler was charged with N-[(2,4-dichloropyrimidin-5-yl)methyl]-N-(4-methoxyphenyl)(phenylamino) carboxamide (78.8 g, 195.4 mmol) (from Example 1e supra) and dichloromethane (120 mL). After cooling to 16° C. with a cold water bath, a solution of sodium hydroxide (14.04 g, 343.9 mmol) in water (28 mL) and aqueous 40% tetrabutylammonium hydroxide solution (1.0 mL, 3.8 mmol) (Aldrich) were added. After stirring at 20–24° C. for 2 hours, an additional portion of aqueous 40% tetrabutylammonium hydroxide solution (0.75 mL, 2.9 mmol) was added. After stirring for 1 hour, a third portion of aqueous 40% tetrabutylammonium hydroxide solution (0.75 mL, 2.9 mmol) was added and the mixture was stirred at room temperature for 2.3 h. TLC analysis indicated essentially reaction was complete. The reaction was then quenched with a mixture of concentrated hydrochloric acid (15 mL) and water (80 mL). The organic layer was separated, washed with water (90 mL), dried over sodium sulfate, and concentrated to a weight of ca. 140 g under reduced pressure. The residue was dissolved in toluene (90 mL) and the solution was concentrated to a weight of 100 g under reduced pressure. The resulting concentrated toluene solution of 7-chloro-3-(4-methoxyphenyl)-1-phenyl-1,3,4-trihydropyrimidino[4,5-d]pyrimid-2-one was used directly in the next step.

Example 1g 3-(4-Methoxyphenyl)-1-phenyl-7-(phenylamino)-1,3,4-trihydropyrimidino[4,5-d]pyrimidin-2-one

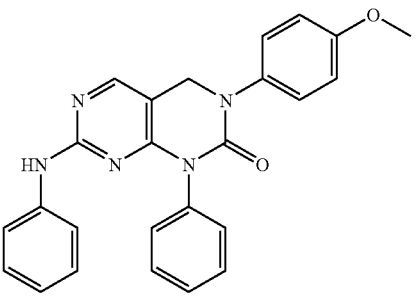

A 500-mL, three-necked flask equipped with a mechanical stirrer, thermometer, condenser, and nitrogen-inlet bubbler was charged with a solution of 7-chloro-3-(4-methoxyphenyl)-1-phenyl-1,3,4-trihydropyrimidino [4,5-d] pyrimidin-2-one (approximately 50 g, ca. 97.7 mmol) (from Example 1f supra) in the toluene solution from the previous step, (70 mL), aniline (22.75 g, 244.3 mmol) (Fluka), and aniline hydrochloride (0.2 g, 1.54 mmol) (Aldrich). The mixture was heated at reflux (at 111–113° C.) for 2 hours to give a slurry. TLC analysis indicated reaction was complete.

After cooling to ca. 80° C., water (50 mL) was added, followed by the addition of hexanes (90 mL). After the resulting suspension was allowed to cool to room temperature over 30 minutes, the solid was collected by filtration, washed with water (100 mL) and methanol (2×45 mL), and dried by suction to give crude 3-(4-methoxyphenyl)-1-phenyl-7-(phenylamino)-1,3,4-trihydropyrimidino[4,5-d]pyrimidin-2-one as a pale-yellow solid; 98.9% pure by HPLC analysis. (Yield 40.5 g, 98%). This material was dissolved in hot acetic acid (50 mL) (ca. 100° C.). After cooling to ca. 70° C., methanol (125 mL) was added over several minutes. The resulting slurry was cooled to 45° C., and the solid was collected by filtration, washed with methanol (50 mL), and dried by suction to give 3-(4-methoxyphenyl)-1-phenyl-7-(phenylamino)-1,3,4-trihydropyrimidino[4,5-d]pyrimidin-2-one as a white solid; 99.49% pure by HPLC analysis. (Yield 38.2 g, 92.3% overall yield from N-[(2,4-dichloropyrimidin-5-yl)methyl]-N-(4-methoxyphenyl)(phenylamino)carboxamide).

Example 1h 3-(4-Methoxyphenyl)-1-phenyl-7-(phenylamino)-1,3,4-trihydropyrimidino[4,5-d]pyrimidin-2-one methanesulfonate salt

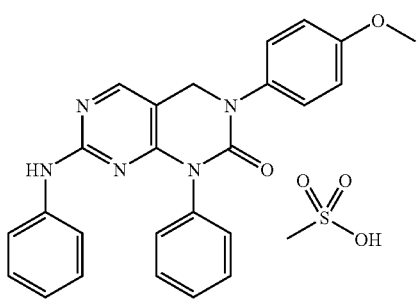

3-(4-Methoxyphenyl)-1-phenyl-7-(phenylamino)-1,3,4-trihydropyrimidino[4,5-d]pyrimidin-2-one (7.50 g, 17.71 mmol) (from Example 1g supra) was dissolved in hot 1,4-dioxane (120 mL) and the solution was filtered through a glass filter. To the clear filtrate was added dropwise a solution of methanesulfonic acid (10 mL) (Aldrich) at room temperature and the mixture was then allowed to stay at −15° C. overnight. The crystalline material formed was collected and washed with 1,4-dioxane, methanol and ether, and dried in vacuo at 85° C. overnight to give 3-(4-methoxyphenyl)-1-phenyl-7-(phenylamino)-1,3,4-trihydropyrimidino[4,5-d]pyrimidin-2-one methanesulfonate salt as a colorless crystal. mp. 245–251° C. (Yield 5.5 g, 59.8%).

Example 2

N-[3-(4-Methoxyphenyl)-2-oxo-1-phenyl(1,3,4-trihydropyrimidino[4,5-d]pyrimidin-7-yl)]-N-phenylacetamide

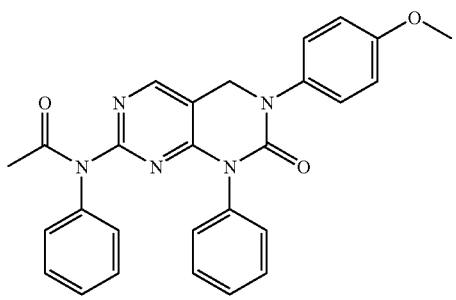

A 250-mL, three-necked flask equipped with a magnetic stirrer, thermometer, condenser, and nitrogen-inlet bubbler was charged with 3-(4-methoxyphenyl)-1-phenyl-7-(phenylamino)-1,3,4-trihydropyrimidino[4,5-d]pyrimidin-2-one (37.90 g, 89.50 mmol) (from Example 1g supra), acetic anhydride (45.3 mL, 481.5 mmol) (J. T. Baker) and N,N-diisopropylethylamine (22.76 mL, 130.7 mmol) (Aldrich). The mixture was heated at reflux (123–127° C.) for 2 hours. TLC analysis indicated essentially reaction was complete. The volatiles were removed at 60° C./18 mmHg to give a solid residue (ca. 69 g), which was dissolved in acetone (45 mL) at 67–70° C. To the resulting solution was slowly added hexanes (50 mL) while maintaining the temperature of the mixture slightly above 54° C., seed crystals of N-[3-(4-methoxyphenyl)-2-oxo-1-phenyl(1,3,4-trihydropyrimidino[4,5-d]pyrimidin-7-yl)]-N-phenylacetamide (ca. 5 mg) were added. The resulting slurry was further diluted with hexanes (50 mL) while maintaining the temperature of the mixture at ca. 53° C. After cooling to room temperature, the solid was collected by filtration, washed with acetone-hexanes (1:2, 3×40 mL), and dried briefly by suction to give crude product (yield 55 g). This material was suspended in hexanes (200 mL) and the resulting slurry was heated to reflux (68–70° C.) for 20 minutes. After cooling to room temperature, the solid was collected by filtration, washed with hexanes (100 mL), and dried by suction to give N-[3-(4-methoxyphenyl)-2-oxo-1-phenyl(1,3,4-trihydropyrimidino[4,5-d]pyrimidin-7-yl)]-N-phenylacetamide as an off-white solid; 98.5% pure by HPLC analysis, containing 1.07% of 3-(4-methoxyphenyl)-1-phenyl-7-(phenylamino)-1,3,4-trihydropyrimidino[4,5-d]pyrimidin-2-one. (Yield 39.4 g, 94.6%).

Example 3

N-[3-(4-methoxyphenyl)-2-oxo-1-phenyl(1,3,4-trihydropyrimidino[4,5-d]pyrimidin-7-yl)]-N-phenylpropanamide

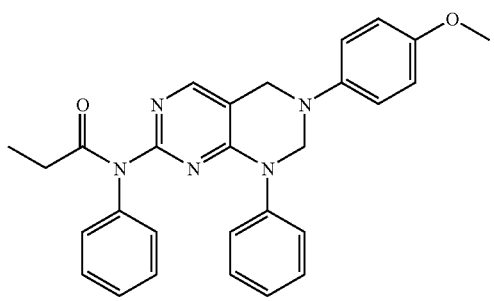

To a solution of 3-(4-methoxyphenyl)-1-phenyl-7-(phenylamino)-1,3,4-trihydropyrimidino[4,5-d]pyrimidin-2-one (304.0 mg, 0.718 mmol) (from Example 1g supra) in pyridine (5 mL) (Fisher) was added propionic anhydride (1.0 mL, 7.8 mmol) (Aldrich) and 4-dimethylaminopyridine (45.0 mg, 0.37 mmol) (Aldrich). The mixture was heated at reflux for 1.5 hours and cooled to room temperature. It was poured into ice (15 g) and stirred for 5 minutes. The mixture was extracted with ethyl acetate (15 mL). The organic layer was washed with water, 5% aqueous hydrochloric acid, and water, dried (Na$_2$SO$_4$), flittered and concentrated under reduced pressure to dryness. The residue was dissolved in dichloromethane and filtered through TLC grade silica gel and washed with ethyl acetate-hexanes (V/V 1:1) and ethyl acetate. The filtrate was concentrated under reduced pressure to dryness. The residue was dissolved in ether and slowly diluted with hexanes. Ether was then removed under reduced pressure. The solid was collected by filtration, washed with hexanes and dried by suction. The solid was dissolved in hot isopropyl acetate (2 mL) and was diluted with hexanes to cloudy. It was allowed to cool in a freezer for 4 days. Resulting suspension was concentrated to dryness under reduced pressure to give N-[3-(4-methoxyphenyl)-2-oxo-1-phenyl(1,3,4-trihydropyrimidino[4,5-d]pyrimidin-7-yl)]-N-phenylpropanamide as a white powder. (Yield 270 mg, 78.4%).

Example 4a (Chloromethoxy)-N-[3-(4-methoxyphenyl)-2-oxo-1-phenyl(1,3,4-trihydropyrimidino[4,5-d]pyrimidin-7-yl)]-N-benzamide

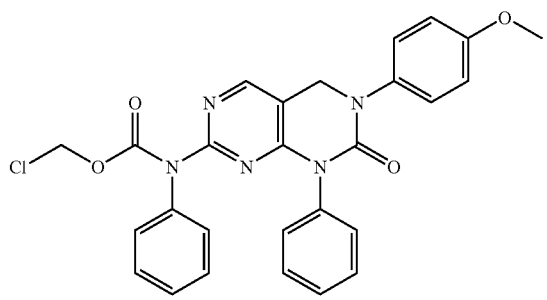

To a solution of 3-(4-methoxyphenyl)-1-phenyl-7-(phenylamino)-1,3,4-trihydropyrimidino[4,5-d]pyrimidin-2-one(3.5 g, 8.26 mmol) (from Example 1g supra) and N,N-diisopropylethylamine (8.63 mL, 49.6 mmol) (Aldrich) in dichloromethane (50 mL) at 0° C., was added fresh chloromethyl chloroformate (2.55 mL, 28.9 mmol) (Lancaster) dropwise. The reaction mixture was stirred at room temperature for 18 hours. The mixture was diluted with dichloromethane and washed with water and brine, dried (MgSO$_4$), filtered and concentrated under reduced pressure. The residue was purified by flash chromatography (Biotage) eluting with 5% ether in dichloromethane to afford crude (chloromethoxy)-N-[3-(4-methoxyphenyl)-2-oxo-1-phenyl(1,3,4-trihydropyrimidino[4,5-d]pyrimidin-7-yl)]-N-benzamide which contained trace amounts of 3-(4-methoxyphenyl)-1-phenyl-7-(phenylamino)-1,3,4-trihydropyrimidino[4,5-d]pyrimidin-2-one and other impurities. This material was used immediately without further purification. (Yield 3.28 g, 77%).

Example 4b

{N-[3-(4-Methoxyphenyl)-2-oxo-1-phenyl(1,3,4-trihydropyrimidino[4,5-d]pyrimidin-7-yl)]-N-phenylcarbamoyloxy}methyl acetate

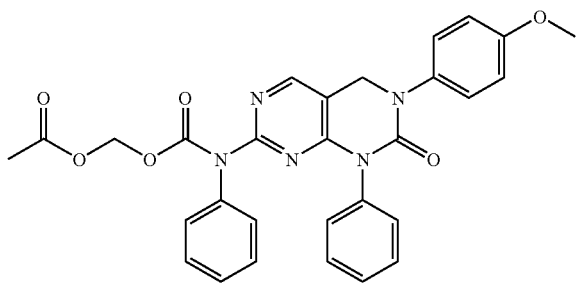

To a solution of (chloromethoxy)-N-[3-(4-methoxyphenyl)-2-oxo-1-phenyl(1,3,4-trihydropyrimidino[4,5-d]pyrimidin-7-yl)]-N-benzamide (3.23 g, 6.32 mmol) (from Example 4a supra) in dimethylformamide (60 mL) was added anhydrous sodium acetate (5.18 g, 63.2 mmol) (Aldrich) and tetrabutyl ammonium hydrogen sulfate (3.22 g, 9.48 mmol) (Aldrich). The mixture was stirred at room temperature for 18 hours, then diluted with water and extracted with ethyl acetate-ether (3×, 1:1). The combined organic phase was washed with water and brine, dried (MgSO$_4$), filtered and concentrated under reduced pressure. The residue was purified by flash chromatography (Biotage) eluting with ethyl acetate-hexanes (1:1 and 3:2) to afford {N-[3-(4-methoxyphenyl)-2-oxo-1-phenyl(1,3,4-trihydropyrimidino[4,5-d]pyrimidin-7-yl)]-N-phenylcarbamoyloxy}methyl acetate as a white foam. (Yield 3.20 g, 93.8%).

Example 5a

{N-[3-(4-Methoxyphenyl)-2-oxo-1-phenyl(1,3,4-trihydropyrimidino[4,5-d]pyrimidin-7-yl)]-N-phenylcarbamoyloxy}methyl 2-dimethylamino) acetate

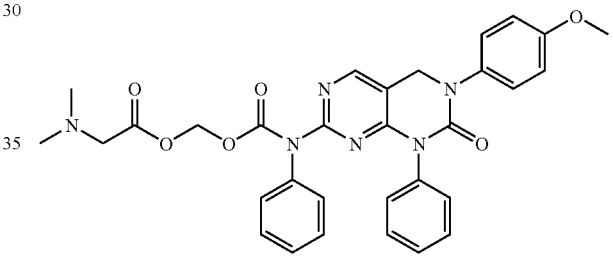

To a solution of (chloromethoxy)-N-[3-(4-methoxyphenyl)-2-oxo-1-phenyl(1,3,4-trihydropyrimidino[4,5-d]pyrimidin-7-yl)]-N-benzammide (300 mg, 0.58 mmol) (from Example 4a supra) in dry tetrahydrofuran (15 mL) under nitrogen was added N,N-dimethylglycine sodium salt (300 mg, 2.1 mmol, the sodium salt was prepared by treatment of the acid (Aldrich) with one equivalent of sodium hydroxide), followed by tetrabutylammonium hydrogen sulfate (329 mg, 0.87 mmol) (Aldrich). The reaction mixture was stirred at room temperature for 72 hours. The mixture was filtered and the solid was purified by flash chromatography (Biotage, 40 S column) with 16% methanol in dichloromethane containing 0.1% triethylamine as the solvent, then 30% methanol in the same solvent system. Combined fractions that contained product was recrystallized from methanol-dichloromethane-hexanes to give {N-[3-(4-methoxyphenyl)-2-oxo-1-phenyl(1,3,4-trihydropyrimidino[4,5-d]pyrimidin-7-yl)]-N-phenylcarbamoyloxy}methyl 2-(dimethylamino)acetate. (Yield 166 mg, 49%).

(M.p.: 172° C.; MS HR-ES [M+H]$^+$–583.2306 (obs) 583.2300 (calc)).

Example 5b

{N-[3-(4-Methoxyphenyl)-2-oxo-1-phenyl(1,3,4-trihydropyrimidino[4,5-d]pyrimidin-7-yl)]-N-phenylcarbamoyloxy}methyl 2-(dimethylamino)acetate hydrochloric acid salt

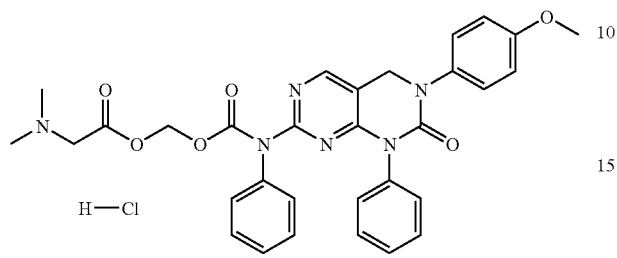

{N-[3-(4-Methoxyphenyl)-2-oxo-1-phenyl(1,3,4-trihydropyrimidino[4,5-d]pyrimidin-7-yl)]-N-phenylcarbamoyloxy}methyl 2-(dimethylamino)acetate (144 mg, 0.247 mmol) (from Example 5a supra) was dissolved in a mixture of tetrahydrofuran (3 mL), acetonitrile (2 mL) and water (15 drops). This was cooled to 0° C. Aqueous 1N hydrochloric acid (272 μL, 0.27 mmol) was added and the reaction was stirred at room temperature for 4 hours. The mixture was diluted with water (10 mL) and the organic solvents were removed under reduced pressure. The aqueous solution was lyophilized to give {N-[3-(4-methoxyphenyl)-2-oxo-1-phenyl(1,3,4-trihydropyrimidino[4,5-d]pyrimidin-7-yl)]-N-phenylcarbamoyloxy}methyl 2-(dimethylamino)acetate hydrochloric acid salt as a white solid.

Example 6a

FMOC-Glycyl Fluoride

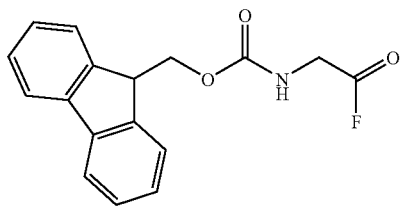

FMOC-Glycine (5.02 g, 16.82 mmol) (Bachem) was dissolved in dichloromethane (85 mL). Pyridine (1.36 mL, 16.82 mmol) (Aldrich) and cyanuric fluoride (2.27 g, 16.82 mmol) (Aldrich) were successively added at room temperature and the mixture was stirred overnight. Ice cold water (100 mL) was added and the resulting slurry was filtered. The filtrate was poured into a separatory funnel and the layers were separated. The organic layer was dried over anhydrous sodium sulfate, filtered, and concentrated under reduced pressure to afford FMOC-glycyl fluoride as a white powder. (Yield 3.67 g, 73%).

Example 6b

2-Amino-N-[3-(4-methoxyphenyl)-2-oxo-1-phenyl(1,3,4-trihydropyrimidino[4,5-d]pyrimidin-7-yl)]-N-phenylacetamide acetic acid salt

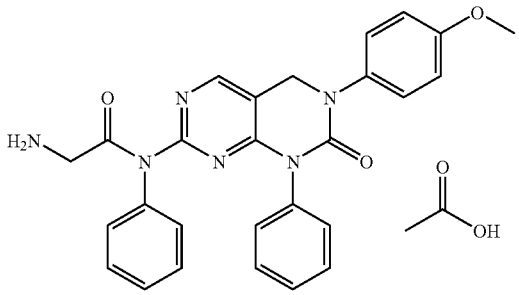

3-(4-Methoxyphenyl)-1-phenyl-7-(phenylamino)-1,3,4-trihydropyrimidino[4,5-d]pyrimidin-2-one (150 mg, 0.35 mmol) (from Example 1g supra) was dissolved in acetonitrile (2 mL). FMOC-glycyl fluoride (265 mg, 0.89 mmol) (from Example 6a supra) was added at room temperature, and the mixture was heated to 120° C. in a microwave apparatus (Smith Synthesizer™) for 30 minutes. The solution was filtered through a plug of activated basic alumina (Alfa Aesar) and the alumina was washed with ethyl acetate. The solution was concentrated under reduced pressure and the residue was dissolved in a mixture of acetonitrile-piperidine (Aldrich) (10:1). After 10 minutes at room temperature, the mixture was concentrated and the residue was triturated with ether—hexanes (1:1). The precipitate was collected by filtration and dried at 45° C. under vacuum. The crude product was purified by reverse phase HPLC (water-acetonitrile gradient, containing 0.1% acetic acid in the solvent) to afford 2-amino-N-[3-(4-methoxyphenyl)-2-oxo-1-phenyl(1,3,4-trihydropyrimidino[4,5-d]pyrimidin-7-]-N-phenylacetamide acid salt. (Yield 63 mg, 34%).

Example 6c

2-Amino-N-[3-(4-methoxyphenyl)-2-oxo-1-phenyl(1,3,4-trihydropyrimidino[4,5-d]pyrimidin-7-yl)]-N-phenylacetamide hydrochloric acid salt

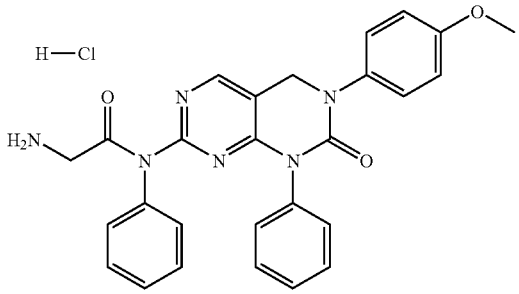

2-Amino-N-[3-(4-methoxyphenyl)-2-oxo-1-phenyl(1,3,4-trihydropyrimidino[4,5-d]pyrimidin-7-yl)]-N-phenylacetamide acetic acid salt (126 mg, 0.24 mmol) (from Example 6b supra) was dissolved in 4N hydrogen chloride in dioxane (4 mL) (Aldrich). The solution was kept at room temperature for 15 minutes, then concentrated to dryness. The residue was triturated with ether and the solid was collected by suction filtration to afford 2-amino-N-[3-(4-methoxy-phenyl)-2-oxo-1-phenyl(1,3,4-trihydropyrimidino

[4,5-d]pyrimid in-7-yl)]-N-phenylacetamide hydrochloric acid salt. (Yield 124 mg, 100%).

Example 7a

FMOC-L-Methionyl Fluoride

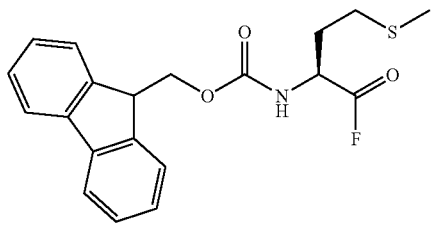

FMOC-L-Methionine (5.00 g, 13.46 mmol) (Bachem) was dissolved in dichloromethane (70 mL). Pyridine (1.09 mL, 13.46 mmol) (Aldrich) and cyanuric fluoride (1.82 g, 13.46 mmol) (Aldrich) were successively added at room temperature and the mixture was stirred overnight. Ice cold water (100 mL) was added and the resulting slurry was filtered. The filtrate was poured into a separatory funnel and the layers were separated. The organic layer was dried over anhydrous sodium sulfate, filtered, and concentrated under reduced pressure to afford FMOC-L-methionyl fluoride as a white powder. (Yield 3.7 g., 74%).

Example 7b (2S)-2-Amino-N-[3-(4-methoxyphenyl)-2-oxo-1-phenyl(1,3,4-trihydropyrimidino[4,5-d]pyrimidino-7-yl)]-4-methylthio-N-phenylbutanamide

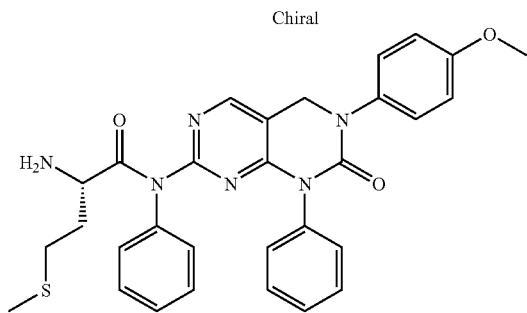

-(4-Methoxyphenyl)-1-phenyl-7-(phenylamino)-1,3,4-trihydropyrimidino[4,5-d]pyrimidin-2-one (150 mg, 0.35 mmol) (from Example 1g supra) was dissolved in acetonitrile (2 mL). FMOC-L-methionyl fluoride (420 mg, 1.12 mmol) (from Example 7a supra) was added at room temperature, and the mixture was heated to 120° C. in a microwave apparatus (Smith Synthesizer™) for 10 minutes. The solution was filtered through a plug of activated basic alumina (Alfa Aesar) and the alumina was washed with ethyl acetate. The filtrate was concentrated under reduced pressure and the residue was purified by reverse phase HPLC to yield the FMOC protected amine (228 mg, 0.29 mmol). This derivative was dissolved in acetonitrile-piperidine (Aldrich) (10:1, 2 mL). After 10 minutes at room temperature, the mixture was concentrated and the residue was triturated with ether-hexanes (1:1). The precipitate was collected by filtration and dried at 45° C. under vacuum to afford (2S)-2-amino-N-[3-(4-methoxyphenyl)-2-oxo-1-phenyl(1,3,4-trihydropyrimidino[4,5-d]pyrimidin-7-y)]-4-methylthio-N-phenylbutanamide as a white solid. (Yield 120 mg, 62%).

Example 7c (2S)-2-amino-N-[3-(4-methoxyphenyl)-2-oxo-1-phenyl(1,3,4-trihydropyrimidino[4,5-d]pyrimidin-7-yl)]-4-methylthio-N-phenylbutanamide acetic acid salt

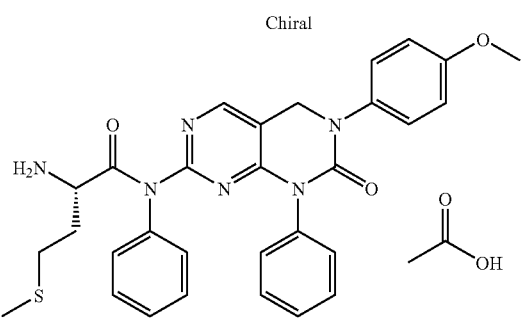

3-(4-Methoxyphenyl)-1-phenyl-7-(phenylamino)-1,3,4-trihydropyrimidino[4,5-d]pyrimidin-2-one (100 mg, 0.24 mmol) (from Example 1g supra) was dissolved in acetonitrile (1.5 mL). FMOC-L-methionyl fluoride (445 mg, 1.18 mmol) (from Example 7a supra) was added at room temperature and the mixture was heated to 120° C. in a microwave apparatus (Smith Synthesizer™) for 10 minutes. The solution was filtered through a plug of activated basic alumina (Alfa Aesar) and the alumina was washed with ethyl acetate. The filtrate was concentrated under reduced pressure and the residue was purified by reverse phase HPLC to yield the FMOC protected amine (42 mg, 0.05 mmol). This derivative was dissolved in acetonitrile-piperidine (Aldrich) (10:1, 1.1 mL). After 10 minutes at room temperature, the mixture was concentrated and the residue was purified by reverse phase HPLC (water-acetonitrile gradient, containing 0.1% acetic acid in the solvent) to afford (2S)-2-amino-N-[3-(4-methoxyphenyl)-2-oxo-1-phenyl(1,3,4-trihydropyrimidino[4,5-d]pyrimidin-7-yl)]-4-methylthio-N-phenylbutanamide acetic acid salt. (Yield 25 mg, 17%).

Example 7d (2S)-2-Amino-N-[3-(4-methoxyphenyl)-2-oxo-1-phenyl(1,3,4-trihydropyrimidino[4,5-d]pyrimidin-7-yl)]-4-methylthio-N-phenylbutanamide hydrochloric acid salt

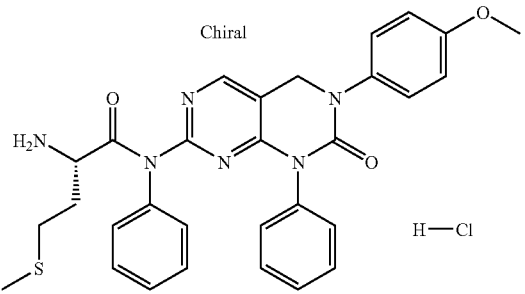

(2S)-2-amino-N-[3-(4-methoxyphenyl)-2-oxo-1-phenyl(1,3,4-trihydropyrimidino [4,5-d]pyrimidin-7-yl)]-4-methylthio-N-phenylbutanamide (350 mg, 0.63 mmol) (from Example 7b supra) was dissolved in 4N hydrogen chloride in dioxane (6 mL) (Aldrich). The homogeneous solution was kept at room temperature for 15 minutes, then concentrated to dryness. The residue was triturated with ether. The precipitate was collected by suction filtration, washed with ether and dried in a vacuum chamber at room temperature to afford (2S)-2-amino-N-[3-(4-methoxyphenyl)-2-oxo-1-phenyl(1,3,4-trihydropyrimidino[4,5-d]pyrimidin-7-yl)]-4-methylthio-N-phenylbutanamide hydrochloric acid salt as an off white solid. (Yield 368 mg, 98%).

Example 8a

FMOC-L-Phenylalanyl Fluoride

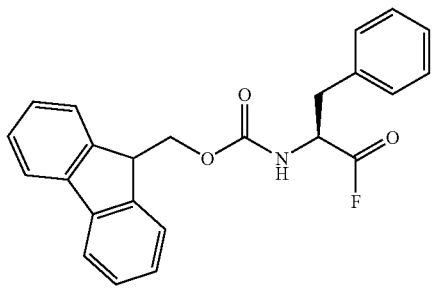

FMOC-L-Phenylalanine (17 g, 44 mmol) (Bachem) was dissolved in dichloromethane (100 mL). Pyridine (3.55 mL, 44 mmol) (Aldrich) and cyanuric fluoride (6 g, 44 mmol) (Aldrich) were successively added at room temperature and the mixture was stirred for 3.5 hours. Ice cold water (300 mL) was added and the resulting slurry was filtered. The filtrate was poured into a separatory funnel and the layers were separated. The organic layer was dried over anhydrous sodium sulfate, filtered and concentrated under reduced pressure to afford FMOC-L-phenylalanyl fluoride as a white powder. (Yield 13.6 g, 80%).

Example 8b (2S)-2-Amino-N-[3-(4-methoxyphenyl)-2-oxo-1-phenyl(1,3,4-trihydropyrimidino[4,5-d]pyrimidin-7-yl)]-3-phenyl-N-phenylpropanamide

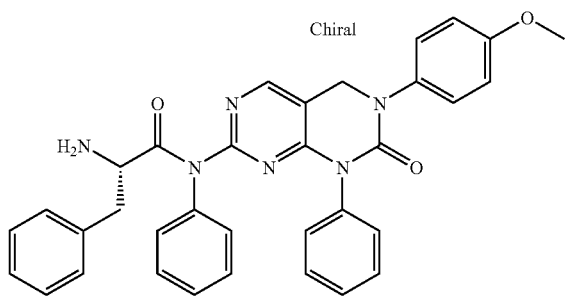

3-(4-Methoxyphenyl)-1-phenyl-7-(phenylamino)-1,3,4-trihydropyrimidino[4,5-d]pyrimidin-2-one (450 mg, 1.05 mmol) (from Example 1g supra) was dissolved in acetonitrile (6 mL). FMOC-L-Phenylalanyl fluoride (2.1 g, 5.25 mmol) (from Example 8a supra) was added at room temperature and the mixture was heated to 120° C. in a microwave apparatus (Smith Synthesizer™) for 10 minutes. The solution was filtered through a plug of activated basic alumina (Alfa Aesar) and the alumina was washed with ethyl acetate. The filtrate was concentrated under reduced pressure and the residue was triturated with 1:1 ether-hexanes. The light orange precipitate was collected by suction filtration and purified by reverse phase HPLC to yield the FMOC protected amine (232 mg, 0.29 mmol). This intermediate was dissolved in 10:1 acetonitrile-piperidine (Aldrich) (5 mL). After 10 minutes at room temperature, the mixture was concentrated and the residue was triturated with 1:1 ether-hexanes. The precipitate was collected by filtration and dried at 45° C. under vacuum to afford (2S)-2-amino-N-[3-(4-methoxyphenyl)-2-oxo-1-phenyl(1,3,4-trihydropyrimidino[4,5-d]pyrimidin-7-yl)]-3-phenyl-N-phenylpropanamide as a white solid. (Yield 110 mg, 20%).

Example 8c (2S)-2-Amino-N-[3-(4-methoxyphenyl)-2-oxo-1-phenyl(1,3,4-trihydropyrimidino[4,5-d]pyrimidin-7-yl)]-3-phenyl-N-phenylpropanamide hydrochloric acid salt

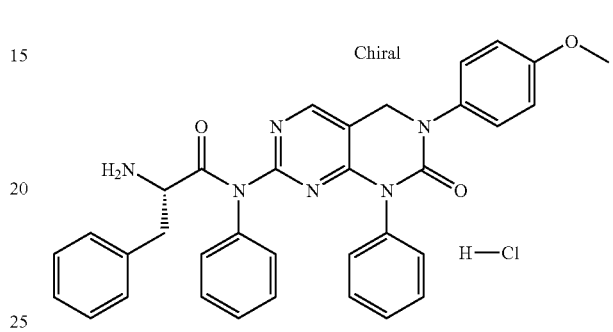

(2S)-2-Amino-N-[3-(4-methoxyphenyl)-2-oxo-1-phenyl(1,3,4-trihydropyrimidino[4,5-d]pyrimidin-7-yl)]-3-phenyl-N-phenylpropanamide (184 mg, 0.32 mmol) (from Example 8b supra) was dissolved in 4N hydrogen chloride in dioxane (4 mL) (Aldrich). The homogeneous solution was kept at room temperature for 15 minutes, then concentrated to dryness. The residue was triturated with ether. The precipitate was collected by suction filtration, and stirred with ethyl acetate overnight, the precipitate was collected by suction filtration, washed with ethyl acetate and dried at 30° C. to afford (2S)-2-amino-N-[3-(4-methoxyphenyl)-2-oxo-1-phenyl(1,3,4-trihydropyrimidino[4,5-d]pyrimidin-7-yl)]-3-phenyl-N-phenylpropanamide hydrochloric acid salt as an off white solid. (Yield 125 mg, 64%).

Example 9a

FMOC-L-Leucyl Fluoride

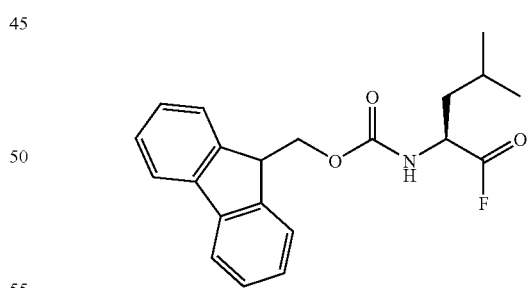

FMOC-L-Leucine (5 g, 14.14 mmol) (Bachem) was dissolved in acetonitrile (70 mL). Pyridine (1.14 mL, 14.14 mmol) (Aldrich) and cyanuric fluoride (1.91 g, 14.14 mmol) (Aldrich) were successively added at room temperature and the mixture was stirred overnight. Ice cold water (300 mL) was added and the resulting slurry was filtered. The filtrate was poured into a separatory funnel and the layers were separated. The organic layer was dried over anhydrous sodium sulfate, filtered and concentrated under reduced pressure to afford FMOC-L-leucyl fluoride as a white powder. (Yield 4.57 g, 91%).

Example 9b (2S)-2-Amino-N-[3-(4-methoxyphenyl)-2-oxo-1-phenyl(1,3,4-trihydropyrimidino[4,5-d]pyrimidin-7-yl)]-4-methyl-N-phenylpropanamide acetic acid salt

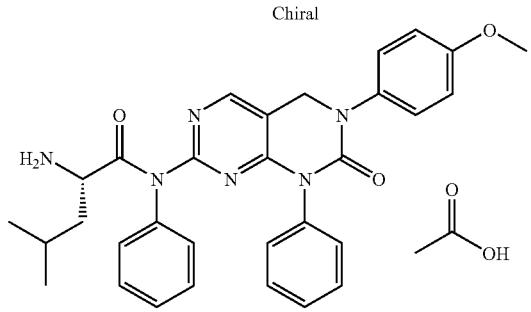

3-(4-Methoxyphenyl)-1-phenyl-7-(phenylamino)-1,3,4-trihydropyrimidino[4,5-d]pyrimidin[4,5-d]pyrimidin-2-one (400 mg, 0.93 mmol) (from Example 1g supra) was dissolved in acetonitrile (4.5 mL). FMOC-L-Leucyl fluoride (1.68 g, 4.72 mmol) (from Example 9a supra) was added at room temperature and the mixture was heated to 120° C. in a microwave apparatus (Smith Synthesizer™) for 10 minutes. The solution was filtered through a plug of activated basic alumina (Alfa Aesar) and the alumina was washed with ethyl acetate. The filtrate was concentrated under reduced pressure and the residue was purified by reverse phase HPLC to yield the FMOC protected amine (323 mg, 0.43 mmol). This intermediate was dissolved in 10:1 acetonitrile-piperidine (Aldrich) (4 mL). After 10 minutes at room temperature, the mixture was concentrated and the residue was triturated with 1:1 ether-hexanes. The precipitate was collected by filtration and dried at 45° C. under vacuum and purified by reverse phase HPLC (water acetonitrile gradient, containing 0.1% acetic acid in solvent) to afford (2S)-2amino-N-[3-(4-methoxyphenyl)-2-oxo-1-phenyl(1,3,4-trihydropyrimidino[4,5-d]pyrimidin-7-yl)]-4-methyl-N-phenylpentanamide acetic acid salt as a white solid. (Yield 96 mg, 17%).

Example 9c (2S)-2-Amino-N-[3-(4-methoxyphenyl)-2-oxo-1-phenyl(1,3,4-trihydropyrimidino[4,5-d]pyrimidin-7-yl)]-4-methyl-N-phenylpentanamide hydrochloric acid salt

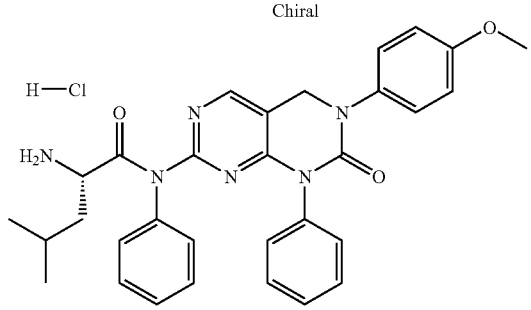

3-(4-Methoxyphenyl)-1-phenyl-7-(phenylamino)-1,3,4-trihydropyrimidino[4,5-d]pyrimidin-2-one (600 mg, 1.42 mmol) (from Example 1g supra) was dissolved in acetonitrile (8 mL). FMOC-L-Leucyl fluoride (629 mg, 1.77 mmol) (from Example 9a supra) was added at room temperature and the mixture was heated to 120° C. in a microwave apparatus (Smith Synthesizer™) for 10 minutes. The solution was filtered through a plug of activated basic alumina (Alfa Aesar) and the alumina was washed with ethyl acetate. The filtrate was concentrated under reduced pressure and the residue was purified by reverse phase HPLC to yield the FMOC protected amine (562 mg, 0.74 mmol). This intermediate was dissolved in 10:1 acetonitrile-piperidine (Aldrich) (4 mL). After 10 minutes at room temperature, the mixture was concentrated and the residue was triturated with ether. The precipitate was collected by filtration and dried at 45° C. then dissolved in 4N hydrogen chloride in dioxane (4 mL) (Aldrich). The solution was concentrated under reduced pressure and the residue was triturated with ether to afford (2S)-2-amino-N-[3-(4-methoxyphenyl)-2-oxo-1-phenyl(1,3,4-trihydropyrimidino[4,5-d]pyrimidin-7-yl)]-4-methyl-N-phenylpentanamide hydrochloric acid salt. (Yield 333 mg, 57%).

Example 10a

N-FMOC-O-t-Butyl-L-Tyrosyl Fluoride

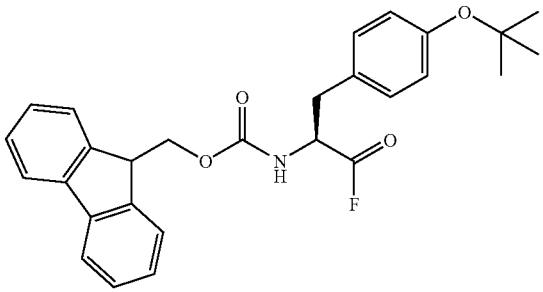

N-FMOC-O-t-Butyl-L-tyrosine (5 g, 10.88 mmol) (Bachem) was dissolved in dichloromethane (50 mL). Pyridine (0.88 mL, 10.88 mmol) (Aldrich) and cyanuric fluoride (1.47 g, 10.88 mmol) (Aldrich) were successively added at room temperature and the mixture was stirred for 5 hours. Ice cold water (100 mL) was added and the resulting slurry was filtered. The filtrate was poured into a separatory funnel and the layers were separated. The organic layer was dried over anhydrous sodium sulfate, filtered and concentrated under reduced pressure to afford N-FMOC-O-t-butyl-L-tyrosyl fluoride as a white powder. (Yield 4.43 g, 88%).

Example 10b (2S)-2-Amino-3-(4-hydroxyphenyl)-N-[3-(4-methoxyphenyl)-2-oxo-1-phenyl(1,3,4-trihydropyrimidino[4,5-d]pyrimidin-7-yl)]-N-phenylpropanamide hydrochloric acid salt

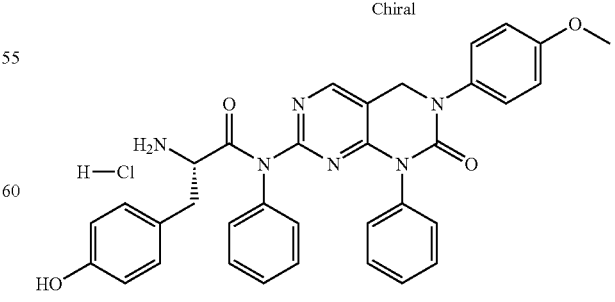

3-(4-Methoxyphenyl)-1-phenyl-7-(phenylamino)-1,3,4-trihydropyrimidino[4,5-d]pyrimidin-2-one (600 mg, 1.41 mmol) (from Example 1g supra) was dissolved in acetonitrile (4.5 mL). N-FMOC-O-t-Butyl-L-tyrosyl fluoride (3.26 g, 7.06 mmol) (from Example 10a supra) was added at room temperature and the mixture was heated to 120° C. in a microwave apparatus (Smith Synthesizer™) for 10 minutes. The solution was filtered through a plug of activated basic alumina (Alfa Aesar) and the alumina was washed with ethyl acetate. The filtrate was concentrated under reduced pressure and the residue was purified by reverse phase HPLC to yield the FMOC-t-butyl ether protected derivative (648 mg, 0.75 mmol). This intermediate was dissolved in 1:1 dichloromethane-trifluoroacetic acid (Aldrich). After 1 hour at room temperature, the mixture was concentrated and the residue was triturated with ether. The precipitate was collected, dried under reduced pressure and treated with 10:1 acetonitrile-piperidine (Aldrich) (5 mL) for 1 hour. The solution was concentrated and the solid residue was triturated with 1:1 ether-hexanes. The solid was collected, dried under reduced pressure, and dissolved in 4N hydrogen chloride in dioxane (10 mL) (Aldrich). Concentration followed by precipitation from ether afforded (2S)-2-amino-3-(4-hydroxyphenyl)-N-[3-(4-methoxyphenyl)-2-oxo-1-phenyl(1,3,4-trihydropyrimidino[4,5-d]pyrimidin-7-yl)]-N-phenyl-propanamide hydrochloric acid salt as a yellow solid. (Yield 216 mg, 25%).

Example 11a

Bis-FMOC-L-Lysyl Fluoride

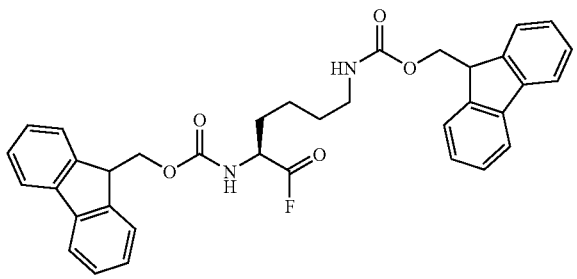

Bis-FMOC-L-Lysine (5 g, 8.46 mmol) (Bachem) was dissolved in dichloromethane (50 mL). Pyridine (0.69 mL, 8.46 mmol) (Aldrich) and cyanuric fluoride (1.14 g, 8.46 mmol) (Aldrich) were successively added at room temperature and the mixture was stirred overnight. Ice cold water (100 mL) was added and the resulting slurry was filtered. The filtrate was poured into a separatory funnel and the layers were separated. The organic layer was dried over anhydrous sodium sulfate, filtered and concentrated under reduced pressure to afford bis-FMOC-L-lysyl fluoride as a white powder. (Yield 1.14 g, 23%).

Example 11b (2S)-2,6-Diamino-N-[3-(4-methoxyphenyl)-2-oxo-1-phenyl(1,3,4-trihydropyrimidino[4,5-d]pyrimidin-7-yl)]-N-phenylhexanamide di-hydrochloric acid salt

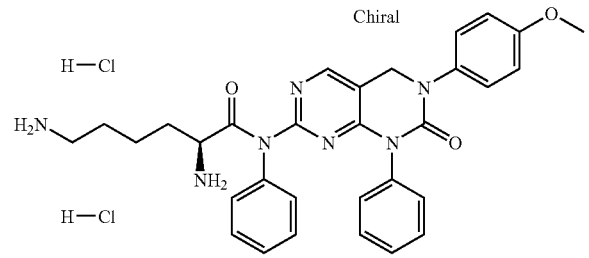

3-(4-Methoxyphenyl)-1-phenyl-7-(phenylamino)-1,3,4-trihydropyrimidino[4,5-d]pyrimidin-2-one (150 mg, 0.35 mmol) (from Example 1g supra) was dissolved in acetonitrile (2 mL). Bis-FMOC-L-Lysyl fluoride (1.05 g, 1.77 mmol) (from Example 11a supra) was added at room temperature and the mixture was heated to 120° C. in a microwave apparatus (Smith Synthesizer™) for 10 minutes. The solution was filtered through a plug of activated basic alumina (Alfa Aesar) and the alumina was washed with ethyl acetate. The filtrate was concentrated under reduced pressure and the residue was purified by reverse phase HPLC to yield the bis-FMOC protected di-amine (36 mg, 0.036 mmol). This intermediate was dissolved in 10:1 acetonitrile-piperidine (Aldrich) (1 mL). After 10 minutes at room temperature, the mixture was concentrated and the residue was triturated with 1:1 ether-hexanes. The solid material was collected by filtration, dried under reduced pressure, then dissolved in 4N hydrogen chloride in dioxane (5 mL) (Aldrich). Concentration under reduced pressure followed by precipitation from ether afforded (2S)-2,6-diamino-N-[3-(4-methoxyphenyl)-2-oxo-1-phenyl(1,3,4-trihydropyrimidino[4,5-d]pyrimidin-7-yl)]-N-phenylhexanamide di-hydrochloric acid salt as a yellow solid. (Yield 25 mg, 10%).

Example 12a

FMOC-L-Tryptophanyl Fluoride

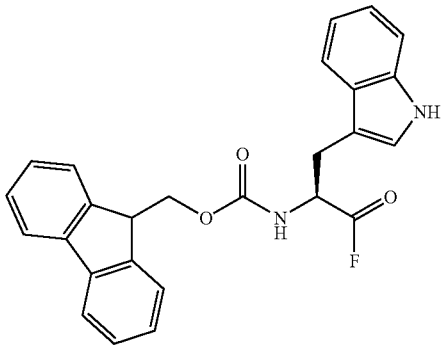

FMOC-L-Tryptophan (5 g, 11.72 mmol) (Bachem) was dissolved in dichloromethane (60 mL). Pyridine (0.95 mL, 11.72 mmol) (Aldrich) and cyanuric fluoride (1.58 g, 11.72 mmol) (Aldrich) were successively added at room temperature and the mixture was stirred for 6.5 hours. Ice cold water (100 mL) was added and the resulting slurry was filtered. The filtrate was poured into a separatory funnel and the layers were separated. The organic layer was dried over anhydrous sodium sulfate, filtered and concentrated under reduced pressure to afford FMOC-L-tryptophanyl fluoride as a beige powder. (Yield 4.36 g, 87%).

Example 12b (2S)-2-Amino-3-indol-3-yl-N-[3-(4-methoxyphenyl)-2-oxo-1-phenyl(1,3,4-trihydropyrimidino[4,5-d]pyrimidin-7-yl)]-N-phenylpropanamide hydrochloric acid salt

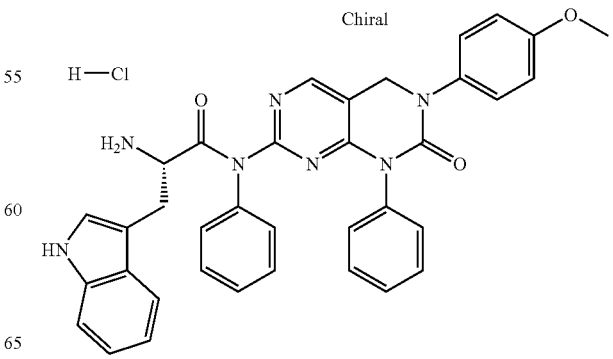

3-(4-Methoxyphenyl)-1-phenyl-7-(phenylamino)-1,3,4-trihydropyrimidino[4,5-d]pyrimidino-[4,5-d]pyrimidin-2-one (600 mg, 1.41 mmol) (from Example 1g supra) was dissolved in acetonitrile (6 mL). FMOC-L-Tryptophanyl fluoride (3.02 g, 7.06 mmol) (from Example 12a supra) was added at room temperature and the mixture was heated to 120° C. in a microwave apparatus (Smith Synthesizer™) for 10 minutes. The solution was filtered through a plug of activated basic alumina (Alfa Aesar) and the alumina was washed with ethyl acetate. The filtrate was concentrated under reduced pressure and the residue was purified by reverse phase HPLC to yield the FMOC protected amine (575 mg, 0.69 mmol). This intermediate was dissolved in 10:1 acetonitrile-piperidine (Aldrich) (3 mL). After 10 minutes at room temperature, the mixture was concentrated and the residue was triturated with 1:1 ether-hexanes. The solid material was collected by filtration, dried under reduced pressure, then dissolved in 4N hydrogen chloride in dioxane (20 mL) (Aldrich). Concentration under reduced pressure followed by precipitation from acetonitrile afforded (2S)-2-amino-3-indol-3-yl-N-[3-(4-methoxyphenyl)-2-oxo-1-phenyl(1,3,4-trihydropyrimidino[4,5-d]pyrimidin-7-yl)]-N-phenylpropanamide hydrochloric acid salt as a yellow solid. (Yield 122 mg, 14%). A second crop of product was obtained after concentration of the mother liquor and triturating with ether. (Yield 285 mg, 31%).

Example 13a
N-FMOC-O-t-Butyl-L-Serinyl Fluoride

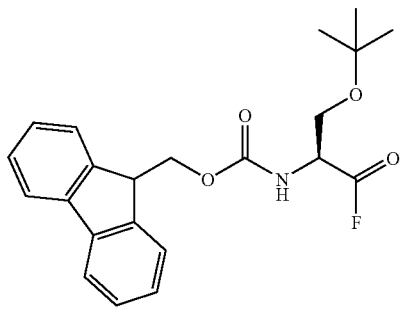

N-FMOC-O-t-Butyl-L-serine (10 g, 26.07 mmol) (Bachem) was dissolved in dichloromethane (135 mL). Pyridine (2.11 mL, 26.07 mmol) (Aldrich) and cyanuric fluoride (3.52 g, 26.07 mmol) (Aldrich) were successively added at room temperature and the mixture was stirred overnight. Ice cold water (100 mL) was added and the resulting slurry was filtered. The filtrate was poured into a separatory funnel and the layers were separated. The organic layer was dried over anhydrous sodium sulfate, filtered and concentrated under reduced pressure to afford N-FMOC-O-t-butyl-L-serinyl fluoride as a colorless oil which solidified upon standing. (Yield 9.79 g., 97%).

Example 13b
(2S)-2-Amino-3-hydroxy-N-[3-(4-methoxyphenyl)-2-oxo-1-phenyl(1,3,4-trihydropyrimidino[4,5-d]pyrimidin-7-yl)]-N-phenylpropanamide

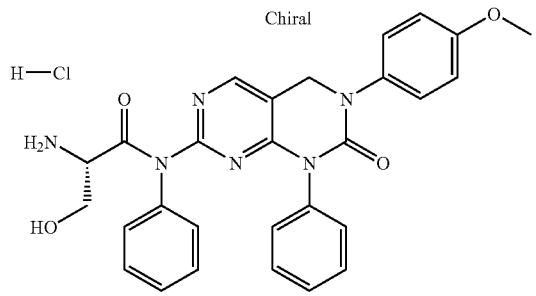

3-(4-Methoxyphenyl)-1-phenyl-7-(phenylamino)-1,3,4-trihydropyrimidino[4,5-d]pyrimidin-2-one (300 mg, 0.71 mmol) (from Example 1g supra) was dissolved in acetonitrile (4 mL). N-FMOC-O-t-Butyl-L-serinyl fluoride (1.38 g, 3.58 mmol) (from Example 13a supra) was added at room temperature and the mixture was heated to 120° C. in a microwave apparatus (Smith Synthesizer™) for 10 minutes. The solution was filtered through a plug of activated basic alumina (Alfa Aesar) and the alumina was washed with ethyl acetate. The filtrate was concentrated under reduced pressure and the residue was purified by reverse phase HPLC to yield the FMOC-t-butyl protected derivative (214 mg, 0.27 mmol). This intermediate was treated with 1:1 dichloromethane-trifluoroacetic acid (Aldrich) (10 mL) for 1 hour. The mixture was concentrated and the residue was purified by reverse phase HPLC (97 mg, 0.13 mmol). This FMOC derivative was dissolved in 10:1 acetonitrile-piperidine (Aldrich) (2 mL). After 10 minutes at room temperature, the mixture was concentrated and the residue was triturated with ether. The solid material was collected by filtration, dried under reduced pressure, then dissolved in 4N hydrogen chloride in dioxane (20 mL) (Aldrich). Concentration under reduced pressure followed by precipitation from ether afforded (2S)-2-amino-3-hydroxy-N-[3-(4-methoxyphenyl)-2-oxo-1-phenyl(1,3,4-trihydropyrimidino[4,5-d]pyrimidin-7-yl)]-N-phenylpropanamide as a yellow solid. (Yield 60 mg, 15%).

Example 14a
FMOC-D-Methionyl Fluoride

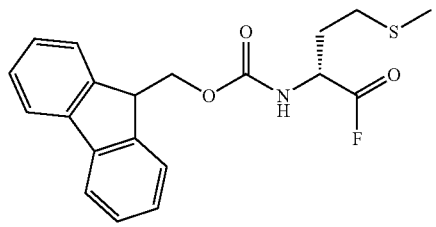

FMOC-D-Methionine (5.00 g, 13.46 mmol) (Bachem) was dissolved in dichloromethane (70 mL). Pyridine (1.09 mL, 13.46 mmol) (Aldrich) and cyanuric fluoride (1.82 g, 13.46 mmol) (Aldrich) were successively added at room temperature and the mixture was stirred for 4 hours. Ice cold water (100 mL) was added and the resulting slurry was filtered. The filtrate was poured into a separatory funnel and the layers were separated. The organic layer was dried over anhydrous sodium sulfate, filtered, and concentrated under reduced pressure to afford FMOC-D-methionyl fluoride as a white powder. (Yield 3.7 g., 74%).

Example 14b
(2R)-2-Amino-N-[3-(4-methoxyphenyl)-2-oxo-1-phenyl(1,3,4-trihydropyrimidino[4,5-d]pyrimidin-7-yl)]-4-methylthio-N-phenylbutanamide hydrochloric acid salt

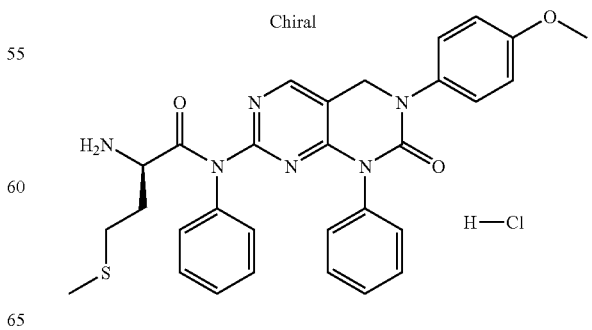

3-(4-Methoxyphenyl)-1-phenyl-7-(phenylamino)-1,3,4-trihydropyrimidino[4,5-d]pyrimidin-2-one (300 mg, 0.71 mmol) (from Example 1g supra) was dissolved in acetonitrile (4 mL). FMOC-D-Methionyl fluoride (1.32 g, 3.54 mmol) (from Example 14a supra) was added at room temperature and the mixture was heated to 120° C. in a microwave apparatus (Smith Synthesizer™) for 10 minutes. The solution was filtered through a plug of activated basic alumina (Alfa Aesar) and the alumina was washed with ethyl acetate. The filtrate was concentrated under reduced pressure and the residue was purified by reverse phase HPLC to yield the FMOC protected amine (242 mg, 0.31 mmol). This intermediate was dissolved in 10:1 acetonitrile-piperidine (Aldrich) (5 mL). After 1 hour at room temperature, the mixture was concentrated and the residue was triturated with ether. The precipitate was collected by filtration, purified by reverse phase HPLC, then dissolved in 4N hydrogen chloride in dioxane (10 mL) (Aldrich) for 30 minutes. The homogeneous solution was concentrated under reduced pressure and the residue was triturated with ether. The precipitate was collected by suction filtration and dried under reduced pressure to afforded (2R)-2-amino-N-[3-(4-methoxyphenyl)-2-oxo-1-phenyl(1,3,4-trihydropyrimidino[4,5-d]pyrimidin-7-yl)]-4-methylthio-N-phenylbutanamide hydrochloric acid salt as a beige solid. (Yield 20 mg, 5%).

Example 15

{N-[3-(4-methoxyphenyl)-2-oxo-1-phenyl(1,3,4-trihydropyrimidino[4,5-d]pyrimidin-7-yl)]-N-phenylcarbamoyloxy}methyl piperidine-4-carboxylate trifluoroacetic acid salt

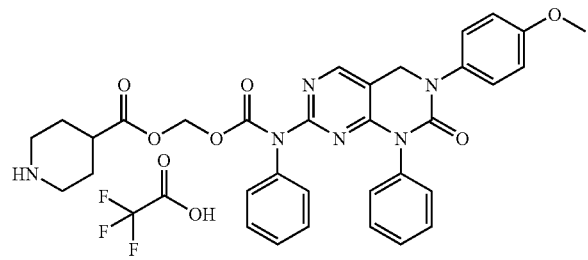

To a solution of (chloromethoxy)-N-[3-(4-methoxyphenyl)-2-oxo-1-phenyl(1,3,4-trihydropyrimidino[4,5-d]pyrimidin-7-yl)]-N-benzamide (200 mg, 0.39 mmol) (from Example 4a supra) dissolved in dry tetrahydrofuran under a nitrogen atmosphere was added BOC-isonipecotic acid sodium salt (356 mg, 1.4 mmol) [the sodium salt was prepared by treatment of the acid (Bachem) with one equivalent of NaOH], followed by tetrabutylammonium hydrogen sulfate (220 mg, 0.582 mmol) (Aldrich). The reaction was stirred at room temperature for 22 hours. TLC showed starting material was still present. Another portion of BOC-isonipecotic acid sodium salt (178 mg, 0.7 mmol) and tetrabutylammonium hydrogen sulfate (110 mg, 0.75 mmol) were added and the reaction was stirred at room temperature for an additional 23 hours. The solvent was blown off with a stream of nitrogen and the crude reaction mixture was partitioned between dichloromethane and water. The organic layer was washed with water and brine and dried over sodium sulfate, then filtered and concentrated under reduced pressure. The protected intermediate was purified by flash chromatography (Biotage, 40 S column) with 10% methanol in dichloromethane, then 15, and 20% as solvent to afford the BOC protected product. (Yield 259 mg, 94%).

The BOC protected product (235 mg, 0.33 mmol) was dissolved in a mixture of dry dichloromethane (7.5 mL) and trifluoroacetic acid (2 mL) and stirred at room temperature for 3 hours. The reaction mixture was concentrated under a stream of nitrogen. The residue was purified by flash chromatography (Biotage, 12 S column) with 20% then 30% methanol in dichloromethane to afford {N-[3-(4-methoxyphenyl)-2-oxo-1-phenyl(1,3,4-trihydropyrimidino[4,5-d]pyrimidin-7-yl)]-N-phenylcarbamoyloxy}methyl piperidine-4-carboxylate trifluoroacetic acid salt. (Yield 121 mg, 50%). The product was recrystallized from dichloromethane-ether. (Mp-88–90° C.).

Example 16

N-[3-(4-Methoxyphenyl)-2-oxo-1-phenyl(1,3,4-trihydropyrimidino[4,5-d]pyrimidin-7-yl)]-N-phenylpentanamide

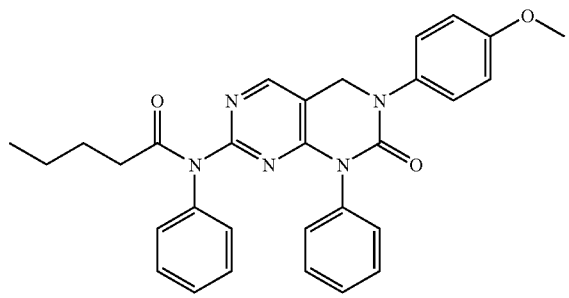

To a solution of 3-(4-methoxyphenyl)-1-phenyl-7-(phenylamino)-1,3,4-trihydropyrimidino[4,5-d]pyrimidin-2-one (0.20 g, 0.47 mmol) (from Example 1g supra) in dry dichloromethane (10 mL) under argon was added valeryl chloride (0.14 mL, 1.18 mmol) (Aldrich) and N,N-diisopropylethylamine (0.41 mL, 2.36 mmol) (Aldrich). The reaction mixture was stirred at room temperature for 1 day. The mixture was then diluted with ethyl acetate and washed with aqueous 1N HCl solution, water, saturated aqueous sodium carbonate solution and brine, dried (MgSO$_4$), filtered and concentrated. The residue was purified by flash chromatography eluting with ethyl acetate/hexanes (3:2, V/V) to afford N-[3-(4-methoxyphenyl)-2-oxo-1-phenyl(1,3,4-trihydropyrimidino[4,5-d]pyrimidin-7-yl)]-N-phenylpentanamide as a white foam. (Yield 0.23 g, 96%).

Example 17

N-[3-(4-Methoxyphenyl)-2-oxo-1-phenyl(1,3,4-trihydropyrimidino[4,5-d]pyrimidin-7-yl)]-N-phenylbutanamide

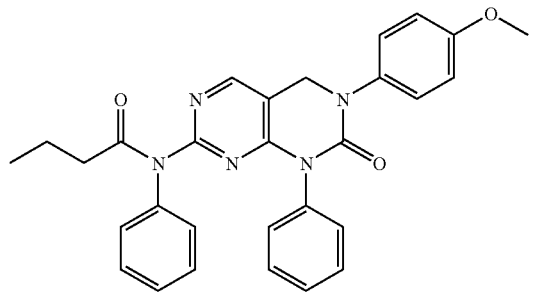

To a solution of 3-(4-methoxyphenyl)-1-phenyl-7-(phenylamino)-1,3,4-trihydropyrimidino[4,5-d]pyrimidin-2-one (0.20g, 0.47 mmol) (from Example 1g supra) in dry dichloromethane (10 mL) under argon was added butyryl chloride (0.12 mL, 1.18 mmol) (Aldrich) and N,N-diisopropylethylamine (0.41 mL, 2.36 mmol) (Aldrich). The reaction mixture was stirred at room temperature for 4 hours. The mixture was then diluted with ethyl acetate and washed with aqueous 1 N HCl solution, water, saturated aqueous sodium carbonate solution and brine, dried (MgSO$_4$), filtered and concentrated. The residue was purified by flash chromatography eluting with ethyl acetate/hexanes (3:2, V/V) to afford N-[3-(4-methoxyphenyl)-2-oxo-1-phenyl(1,3,4-trihydropyrimidino[4,5-d]pyrimidin-7-yl)]-N-phenylbutanamide as a white foam. (Yield 0.23 g, 100%).

Example 18

7-[(4-Hydroxyphenyl)amino]-3-(4-methoxyphenyl)-1-phenyl-1,3,4-trihydropyrimidino[4,5-d]pyrimidin-2-one

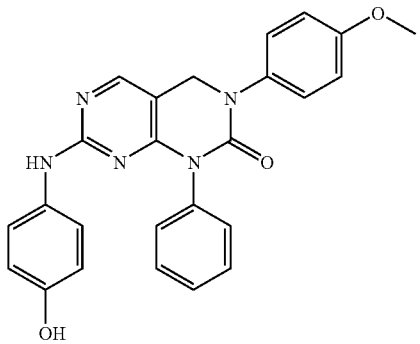

A solution of 7-chloro-3-(4-methoxyphenyl)-1-phenyl-1,3,4-trihydropyrimidino[4,5-d]pyrimidin-2-one (0.15 g, 0.41 mmol) (from Example 1f supra) and 4-amino-phenol (57.8 mg, 0.53 mmol) (Aldrich) in 2-propanol (3.5 mL) was placed in a microwave reactor (Smith Synthesizer™). The reaction mixture was heated at 160° C. for 10 minutes. The precipitate formed was filtered, washed with ethanol and dried to afford 7-[(4-hydroxyphenyl)amino]-3-(4-methoxyphenyl)-1-phenyl-1,3,4-trihydropyrimidino[4,5-d]pyrimidin-2-one. (Yield 0.12g, 67%).

Example 19a

1-Nitro-4-(1,1,2,2-tetramethyl-1-silapropoxy)benzene

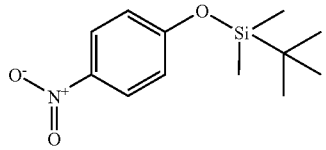

To a solution of 4-nitrophenol (5.0 g, 35.9 mmol) (Aldrich) in dimethylformamide (50 mL) was added imidazole (3.18 g, 46.7 mmol) (Aldrich) and t-butyldimethylsilyl chloride (6.49 g, 43.1 mmol) (Avocado Research Chemicals Ltd.). The reaction mixture was stirred at room temperature for 1 day. TLC analysis showed starting material was still present. Another portion of t-butyldimethylsilyl chloride (1.0 g, 6.63 mmol) was added and the mixture was stirred at room temperature for another 1 day. The reaction mixture was concentrated under reduced pressure. The residue was dissolved in ethyl acetate (200 mL) and washed with a mixture of water (100 mL) and aqueous 1N HCl (80 mL). The organic layer was then washed with water, saturated aqueous sodium bicarbonate solution and brine, dried (MgSO$_4$), filtered and concentrated. The residue was purified by flash chromatography eluting with ethyl acetate/hexanes (1:9, V/V) to afford 1-nitro-4-(1,1,2,2-tetramethyl-1-silapropoxy)benzene. (Yield 7.8 g, 86%).

Example 19b 4-(1,1,2,2-Tetramethyl-1-silapropoxy)phenylamine

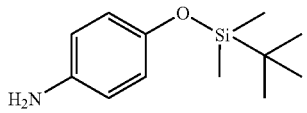

A solution of 1-nitro4-(1,1,2,2-tetramethyl-1-silapropoxy)benzene (7.8 g, 30.8 mmol) (from Example 19a supra) and 10% Pd/C (0.70 g) (Aldrich) in ethyl acetate (100 mL) was hydrogenated for 1 day. The reaction mixture was filtered though Celite® and concentrated. The residue was purified by flash chromatography eluting with ethyl acetate/hexanes (1:9 V/N)) to afford 4-(1,1,2,2-tetramethyl-1-silapropoxy)phenylamine. (Yield 6.7 g, 97%).

Example 19c 3-(4-Methoxyphenyl)-1-phenyl-7-{[4-(1,1,2,2-tetramethyl-1-silapropoxy) phenyl]amino}-1,3,4-trihydropyrimidino[4,5-d]pyrimidin-2-one

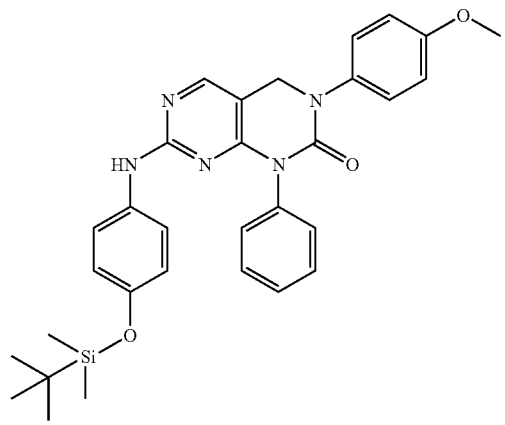

A solution of 7-chloro-3-(4-methoxyphenyl)-1-phenyl-1,3,4-trihydropyrimidino[4,5-d]pyrimidino[4,5-d]pyrimidin-2-one (0.20 g, 0.55 mmol) (from Example 1f supra) and 4-(1,1,2,2-tetramethyl-1-silapropoxy)phenylamine (0.16 g, 0.71 mmol) (from Example 19b supra) in 2-propanol (4 mL) was placed in a microwave reactor (Smith Synthesizer™). The reaction mixture was heated at 160° C. for 10 minutes. The precipitate formed was filtered, washed with 2-propanol and dried to afford 3-(4-methoxyphenyl)-1-phenyl-7-{[4-(1,1,2,2-tetramethyl-1-silapropoxy)phenyl]amino}-1,3,4-trihydropyrimidino[4,5-d]pyrimidin-2-one. (Yield 0.28 g, 93%).

Example 19d

N-[3-(4-Methoxyphenyl)-2-oxo-1-phenyl(1,3,4-trihydropyrimidino[4,5-d]pyrimidin-7-yl)]-N-[4-(1,1,2,2-tetramethyl-1-silapropoxy)phenyl]acetamide

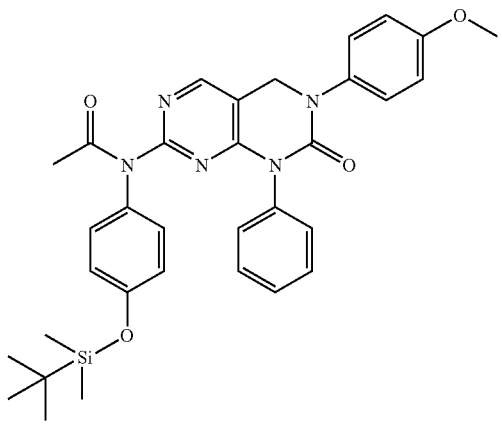

To a solution of 3-(4-methoxyphenyl)-1-phenyl-7-{[4-(1,1,2,2-tetramethyl-1-silapropoxy)phenyl]amino}-1,3,4-trihydropyrimidino[4,5-d]pyrimidin-2-one (0.28 g, 0.51 mmol) (from Example 19c supra) and N,N-diisopropylethylamine (0.44 mL, 2.55 mmol) (Aldrich) in dry dichloromethane (10 mL) under argon was added acetyl chloride (0.09 mL, 1.26 mmol) (Aldrich). The reaction mixture was stirred at room temperature for 4 hours. The mixture was diluted with dichloromethane and washed with water and brine, dried (MgSO₄), filtered and concentrated. The residue was purified by flash chromatography eluting with ethyl acetate/hexanes (3:7, then 2:3, V/V)) to afford N-[3-(4-methoxyphenyl)-2-oxo-1-phenyl(1,3,4-trihydropyrimidino[4,5-d]pyrimidin-7-yl)]-N-[4-(1,1,2,2-tetramethyl-1-silapropoxy)phenyl]acetamide. (Yield 0.18 g, 60%).

Example 19

N-(4-Hydroxyphenyl)-N-[3-(4-methoxyphenyl)-2-oxo-1-phenyl(1,3,4-trihydropyrimidino[4,5-d]pyrimidin-7-yl)]acetamide

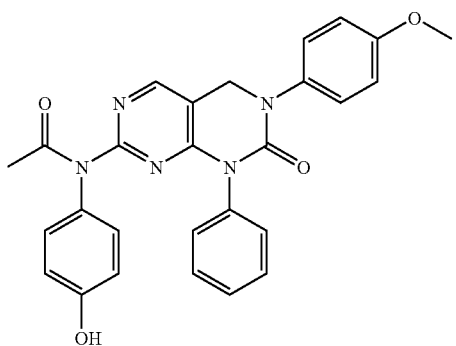

To a solution of N-[3-(4-methoxyphenyl)-2-oxo-1-phenyl(1,3,4-trihydropyrimidino[4,5-d]pyrimidin-7-yl)]-N-[4-(1,1,2,2-tetramethyl-1-silapropoxy)phenyl] acetamide (0.17 g, 0.29 mmol) (from Example 19d supra) in dry tetrahydrofuran (5 mL) under argon was added tetrabutylammonium fluoride (1.0 M solution in tetrahydrofuran, 0.43 mL, 0.43 mmol) (Aldrich). The reaction mixture was stirred at room temperature for 4 hours. The mixture was concentrated, and the residue was purified by flash chromatography eluting with ethyl acetate/hexanes (4:1 V/V)) and ethyl acetate to afford N-(4-hydroxyphenyl)-N-[3-(4-methoxyphenyl)-2-oxo-1-phenyl(1,3,4-trihydropyrimidino[4,5-d]pyrimidin-7-yl)]acetamide. (Yield 73 mg, 52%).

Example 20

3-(4-Methoxyphenyl)-7-[(4-methoxyphenyl)amino]-1-phenyl-1,3,4-trihydropyrimidino[4,5-d]pyrimidin-2-one

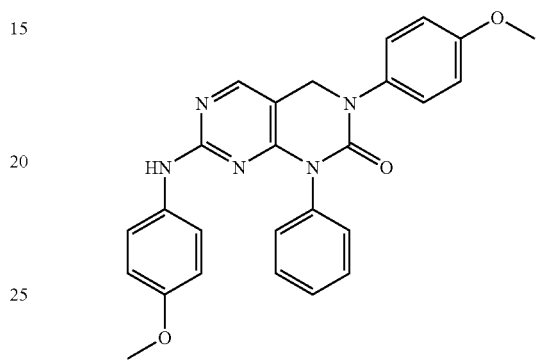

A solution of 7-chloro-3-(4-methoxyphenyl)-1-phenyl-1,3,4-trihydropyrimidino[4,5-d]pyrimidin-2-one (0.15 g, 0.41 mmol) (from Example 1f supra) and p-anisidine (65 mg, 0.53 mmol) (Aldrich) in 2-propanol (3.5 mL) was placed in a microwave reactor (Smith Synthesizer™). The reaction mixture was heated at 160° C. for 10 minutes. The precipitate formed was filtered, washed with 2-propanol and dried to afford 3-(4-methoxyphenyl)-7-[(4-methoxyphenyl)amino]-1-phenyl-1,3,4-trihydropyrimidino[4,5-d]pyrimidin-2one. (Yield 0.18 g, 97%).

Example 21

N-(4-methoxyphenyl)-N-[3-(4-methoxyphenyl)-2-oxo-1-phenyl(1,3,4-trihydropyrimidino[4,5-d]pyrimidin-7-yl)]acetamide

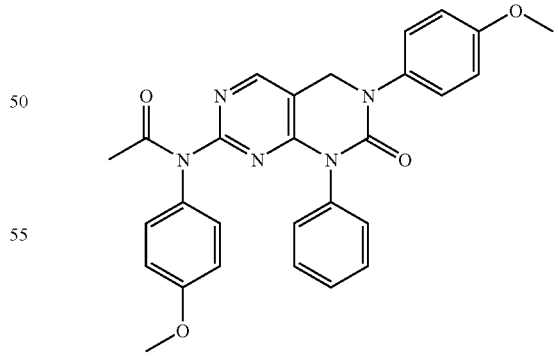

To a solution of 3-(4-methoxyphenyl)-7-[(4-methoxyphenyl)amino]-1-phenyl-1,3,4-trihydropyrimidino[4,5-d]pyrimidin-2-one (0.10 g, 0.22 mmol) and N,N-diisopropyl-ethylamine (0.19 mL, 1.1 mmol) (from Example 20 supra) in dry dichloromethane (10 mL) under argon was added acetyl chloride (0.04 mL, 0.55 mmol) (Aldrich). The reaction mixture was stirred at room temperature overnight. The mixture was then diluted with dichloromethane and washed with water and brine, dried (MgSO$_4$), filtered and concentrated. The residue was purified by flash chromatography eluting with ethyl acetate/hexanes (7:3 V/V)) to afford N-(4-methoxyphenyl)-N-[3-(4-methoxyphenyl)-2-oxo-1-phenyl(1,3,4-trihydro-pyrimidino[4,5-d]pyrimidin-7-yl)]acetamide. (Yield 24 mg, 22%).

Antiproliferative Activity

The antiproliferative activity of the compounds of the invention is demonstrated below in Examples 22 and 23. These activities indicate that the compounds of the present invention are useful in treating cancer, in particular solid tumors such as breast and colon tumors.

Example 22

Kinase Assays

To determine inhibition of KDR, FGFR, EGFR, and PDGFR activity, kinase assays were conducted using an HTRF (Homogeneous Time Resolved Fluorescence) assay. This assay is described in A. J. Kolb et. al., Drug Discovery Today, 1998, 3(7), p 333.

Prior to kinase reaction, recombinant EEE-tagged KDR was activated in the presence of activation buffer (50 mM HEPES, pH 7.4, 1 mM DTT, 10% glycerol, 150 mM NaCl, 0.1 mM EDTA, 26 mM MgCl$_2$, and 4 mM ATP). The enzyme was incubated at 4° C. for 1 hour.

Kinase activity assays were performed in 96-well polypropylene plates (Falcon) with a total volume of 90 µL in each well. Each well contained 1 µM KDR substrate (Biotin-EEEEYFELVAKKKK), 1 nM activated KDR, and a test compound with one of 8 assay concentrations ranging from 100 µM to 128 pM (1:5 serial dilution). The kinase activity assay was done in the presence of 100 mM HEPES, pH 7.4, 1 mM DTT, 0.1 mM Na$_2$VO$_4$, 25 mM MgCl$_2$, 50 mM NaCl (from KDR stock solution), 1% DMSO (from compound), 0.3 mM ATP (at K$_m$ concentration) and 0.02% BSA. The reaction was incubated at 37° C. for 30 minutes. To stop the KDR reaction, 72 µL of reaction mixture was transferred into a STOP plate containing 18 µL of revelation buffer (20 mM EDTA, 50 mM HEPES, pH 7.4, 0.02% BSA, 10 nM Eu-labelled anti-pY antibody (final conc. 2 nM), and 100 nM streptavidin (final conc. 20 nM)). After mixing, 35 µL of solution was transferred into duplicate wells of a 384-well black plate (Costar), and read at 615/665 nm on a Wallac Victor 5 reader.

FGFR, EGFR, and PDGFR activity assays were carried out as described above for the KDR activity assay with the following differences. GST-tagged FGFR enzyme was activated at room temperature for 1 hour in the following activation buffer: 100 mM HEPES, pH 7.4, 50 mM NaCl, 20 mM MgCl$_2$, and 4 mM ATP. The kinase activity assay was performed with 1 µM substrate (Biotin-EEEEYFELV), 1.5 nM activated FGFR, and test compound in the presence of 100 mM HEPES, 1 mM DTT, 0.4 mM MgCl$_2$, 0.4 mM MnCl$_2$, 50 mM NaCl, 1% DMSO, 10 µM ATP (K$_m$=8.5 µM for FGFR), 0.1 mM Na$_2$VO$_4$, and 0.02% BSA, in a total volume of 90 µL. The rest of the assay was performed in the same manner as KDR assay.

The EGFR kinase activity assay was performed with 1 µM substrate (Biotin-EEEEYFELV), 1.5 nM EGFR, test compounds, 100 mM HEPES, pH 7.4, 1 mM DTT, 5 mM MgCl$_2$, 2 mM MnCl$_2$, 1% DMSO, 0.5 µM ATP (K$_m$ for EGFR), 0.1 mM Na$_2$VO$_4$, and 0.02% BSA. The rest of the assay was performed in the same manner as the KDR assay.

The PDGFR kinase activity assay was performed with 1 µM substrate (Biotin-EEEEYFELV), 1.0 nM PDGFR, test compounds, 100 mM HEPES, pH 7.4, 1 mM DTT, 5 mM MgCl$_2$, 2 mM MnCl$_2$, 1% DMSO, 2.3 µM ATP (K$_m$ for PDGFR), 0.1 mM Na$_2$VO$_4$, and 0.02% BSA. The rest of the assay was performed in the same manner as the KDR assay.

Compound IC$_{50}$ values were determined from duplicate sets of data, and calculated by using Excel and fitting data to equation Y=[(a−b)/{1+(X/c)$^d$}]+b, where a and b are enzyme activity in the presence of no test inhibitor compound and an infinite amount of inhibitor test compound, respectively, c is the IC$_{50}$ and d is the hill constant of the compound response. The IC$_{50}$ value is the concentration of test compound that reduces by 50% the enzyme activity under the test conditions described.

The results of the foregoing in vitro experiments, including IC$_{50}$ values, are set forth in Table 1 below.

TABLE 1

| | | IC$_{50}$ of enzyme inhibition | | | |
|---|---|---|---|---|---|
| | | KDR | FGFR | EGFR | PDGFR |
| Example | ERN | | IC$_{50}$ (µM) | | |
| 1g | RO0329774-000 | .044 | .190 | .360 | .130 |
| 1h | RO0329774-003 | .076 | .170 | .350 | .150 |
| 18 | RO4390430-000 | .029 | .110 | .130 | .064 |
| 20 | RO4400673-000 | .024 | .091 | .180 | .082 |

Example 23

VEGF and FGF-Stimulated HUVEC Proliferation Assays

The antiproliferative activity of test compounds of this invention in cell-based assays was evaluated by BrdU assay using the BrdU kit (Roche Biochemicals 1-647-229). Human umbilical vein endothelial cells (Clonetics CC-2519) were cultured in EGM-2 (Clonetics CC-3162) medium and seeded at 10000 cells per well in a volume of 200 µL of EGM-2 (Clonetics CC-3162) media in a 96-well flat bottom plates (Costar 3595) overnight. After 24 hours of growth at 37° C. with 5% CO$_2$, the incubation media was removed slowly by aspiration and the content of each well was washed with 300 µL pre-warmed EBM-2 (Clonetics CC-3156) containing 50 µg per mL of gentamycin and 50 ng per mL of amphotercin-B (Clonetics CC-4083). Subsequently, the remaining media was again aspirated and replaced with 160 µL per well of serum starvation media (EBM-2 supplemented with 1% heat inactivated FBS (Clonetics CC-4102), 50 µg per mL gentamycin and 50 ng per mL of amphotercin-B (Clonetics CC-4083), 10 units per mL of Wyeth-Ayerst heparin (NDC0641-0391-25), and 2 mM L-glutamine (GIBCO 25030-081). After serum starving the cells for 24 hours, 20 µL of test compound at 10× test concentration in serum starvation medium with 2.5% DMSO was added to the appropriate wells. The control wells contained 20 µL of serum starvation medium with 2.5% DMSO. Plates were returned to the incubator for 2 hours. After pre-incubating the cells with the test compounds for 2 hours, 20 µL of growth factors at 10×assay concentration diluted in serum starvation media, FGF at 50 ng per mL, or VEGF (R&D systems 293-VE) at 200 ng per mL were added. The final concentration of FGF in the assay was 5 ng per mL, and the final concentration of VEGF in the assays was 20 ng per mL. The growth factor free control wells had 20 µL per well of serum starvation media with the same amount of BSA as the wells with growth factors. The plates were returned to the incubator for an additional 22 hours.

BrdU ELISA

After 24 hour exposure to the test compounds, the cells were labeled with BrdU (Roche Biochemicals 1-647-229), by adding 20 µL per well of BrdU labeling reagent that has been diluted (1:100) in serum starvation medium. The plates were then returned to the incubator for 4 hours. The labeling medium was removed by draining the medium onto paper towels. The cells were fixed and DNA denatured by adding 200 µL of fixation/denaturation solution to each well and incubating at room temperature for 45 minutes. The fixation/denaturation solution was drained onto paper towels and to each well was added 100 µL of anti-BrdU-POD and the wells were incubated for 2 hours at room temperature. The antibody solution was removed and the wells were each washed 3–4 times with 300 µL PBS. 100 µL of the TMB substrate solution was added to each well and the wells were incubated at room temperature for 5–8 minutes. The reaction was then stopped by adding 100 µL per well of 1M phosphoric acid. The plates were read at 450 nm with reference wavelength of 650 nm. The percent inhibition for each test compound was calculated by subtracting the absorbency of the blank (no cells) wells from all wells, then subtracting the division of the average absorbency of each test duplicate by the average of the controls from 1. The final product was then multiplied by 100 (% of inhibition=(1-average absorbency of test duplicate/average of control) 100). The $IC_{50}$ value is the concentration of test compound that inhibits by 50% BrdU labeling, and is a measure of inhibition of cell proliferation. The $IC_{50}$ is determined from the linear regression of a plot of the logarithm of the concentration versus percent inhibition. The $IC_{50}$ values are shown in Table 2 below.

TABLE 2

$IC_{50}$ of VEGF and FGF-Stimulated HUVEC Proliferation Assays

| Example | ERN | HUVEC/VEFG $IC_{50}$ (µM) | HUVEC/bFGFR |
|---|---|---|---|
| 1g | RO0329774-000 | .120 | .310 |
| 1h | RO0329774-003 | .120 | .430 |
| 18 | RO4390430-000 | .063 | .150 |
| 20 | RO4400673-000 | .096 | .350 |

Example 24

Tablet Formulation

| Item | Ingredients | Mg/Tablet | | | | | |
|---|---|---|---|---|---|---|---|
| 1 | Compound A* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound A represents a compound of the invention.

Manufacturing Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 25

Capsule Formulation

| Item | Ingredients | mg/Capsule | | | | |
|---|---|---|---|---|---|---|
| 1 | Compound A* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

Compound A represents a compound of the invention.

Manufacturing Procedure:
1. Mix Items 1, 2 and 3 in a suitable mixer for 15 minutes.
2. Add Items 4 & 5 and mix for 3 minutes.
3. Fill into a suitable capsule.

Example 26

Injection Solution/Emulsion Preparation

| Item | Ingredient | mg/mL |
|---|---|---|
| 1 | Compound A* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 µm filter and fill into vials.

Example 27

Injection Solution/Emulsion Preparation

| Item | Ingredient | mg/mL |
|---|---|---|
| 1 | Compound A* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.

What is claimed is:

1. A compound of formula:

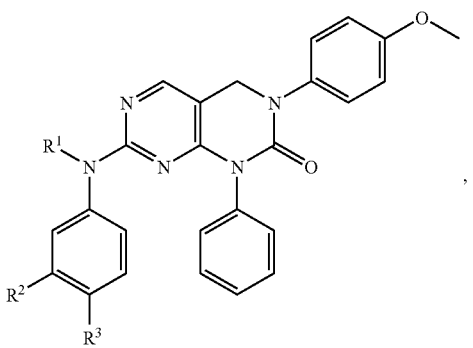

wherein
R¹ is selected from the group
—H,
—COR⁴, and
—COOCHR⁵OCOR⁴;
R² and R³ are independently selected from
—H, and
—OR⁵;
R⁴ is selected from the group
—C$_{1-6}$ alkyl,
-lower alkyl substituted by up to 4 groups independently selected from
—NR⁵R⁶,
—SR⁵,
—OR⁵,
-aryl,
-aryl substituted by up to 2 groups independently selected from
—OR⁵ and C$_{1-4}$ lower alkyl, and
-heteroaryl, and
-heterocycle;
R⁵ and R⁶ are independently selected from
—H, and
—C$_{1-5}$ lower alkyl,
or, alternatively, —NR⁵R⁶ can form a ring having 3 to 7 atoms, said ring optionally including one or more additional N or O atoms:
or the pharmaceutically acceptable salts thereof.

2. The compound of claim 1 wherein R¹ is —COR⁴.

3. The compound of claim 2 wherein R² is H.

4. The compound of claim 3 wherein R³ is H.

5. The compound of claim 4 which is selected from the group:
N-[3-(4-Methoxyphenyl)-2-oxo-1-phenyl(1,3,4-trihydropyrimidino[4,5-d]pyrimid-7-yl)]-N-phenylacetamide;
N-[3-(4-methoxyphenyl)-2-oxo-1-phenyl(1,3,4-trihydropyrimidino[4,5-d]pyrimid-7-yl)]-N-phenylpropanamide;
2-Amino-N-[3-(4-methoxyphenyl)-2-oxo-1-phenyl(1,3,4-trihydropyrimidino[4,5-d]pyrimidin-7-yl)-N-phenylacetamide acetic acid salt;
2-Amino-N-[3-(4-methoxyphenyl)-2-oxo-1-phenyl(1,3,4-trihydropyrimidino[4,5-d]pyrimidin-7-yl)]-N-phenylacetamide hydrochloric acid salt;
(2S)-2-Amino-N-[3-(4-methoxyphenyl)-2-oxo-1-phenyl(1,3,4-trihydropyrimidino[4,5-d]pyrimidin-7-yl)]-4-methylthio-N-phenylbutanamide;
(2S)-2-amino-N-[3-(4-methoxyphenyl)-2-oxo-1-phenyl(1,3,4-trihydropyrimidino[4,5-d]pyrimidin-7-yl)]-4-methylthio-N-phenylbutanamide acetic acid salt;
(2S)-2-Amino-N-[3-(4-methoxyphenyl)-2-oxo-1-phenyl(1,3,4-trihydropyrimidino[4,5-d]pyrimidin-7-yl)]-4-methylthio-N-phenylbutanamide hydrochloric acid salt;
(2S)-2-Amino-N-[3-(4-methoxyphenyl)-2-oxo-1-phenyl(1,3,4-trihydropyrimidino[4,5-d]pyrimidin-7-yl)]-3-phenyl-N-phenylpropanamide;
(2S)-2-Amino-N-[3-(4-methoxyphenyl)-2-oxo-1-phenyl(1,3,4-trihydropyrimidino[4,5-d]pyrimidin-7-yl)]-3-phenyl-N-phenylpropanamide hydrochloric acid salt;
(2S)-2-Amino-N-[3-(4-methoxyphenyl)-2-oxo-1-phenyl(1,3,4-trihydropyrimidino[4,5-d]pyrimidin-7-yl)]-4-methyl-N-phenylpentanamide acetic acid salt;
(2S)-2-Amino-N-[3-(4-methoxyphenyl)-2-oxo-1-phenyl(1,3,4-trihydropyrimidino[4,5-d]pyrimidin-7-yl)]-4-methyl-N-phenylpentanamide hydrochloric acid salt;
(2S)-2-Amino-3-(4-hydroxyphenyl)-N-[3-(4-methoxyphenyl)-2-oxo-1-phenyl(1,3,4-trihydropyrimidino[4,5-d]pyrimidin-7-yl)]-N-phenylpropanamide hydrochloric acid salt;
(2S)-2,6-Diamino-N-[3-(4-methoxyphenyl)-2-oxo-1-phenyl(1,3,4-trihydropyrimidino[4,5-d]pyrimidin-7-yl)]-N-phenylhexanamide di-hydrochloric acid salt;
(2S)-2-Amino-3-indol-3-yl-N-[3-(4-methoxyphenyl)-2-oxo-1-phenyl(1,3,4-trihydropyrimidino[4,5-d]pyrimidin-7-yl)]-N-phenylpropanamide hydrochloric acid salt;
(2S)-2-Amino-3-hydroxy-N-[3-(4-methoxyphenyl)-2-oxo-1-phenyl(1,3,4-trihydropyrimidino[4,5-d]pyrimidin-7-yl)]-N-phenylpropanamide;
(2R)-2-Amino-N-[3-(4-methoxyphenyl)-2-oxo-1-phenyl(1,3,4-trihydropyrimidino[4,5-d]pyrimidin-7-yl)]-4-methylthio-N-phenylbutanamide hydrochloric acid salt;
N-(3-(4-Methoxyphenyl)-2-oxo-1-phenyl(1,3,4-trihydropyrimidino[4,5-d]pyrimidin-7-yl)]-N-phenylpentanamide; and
N-[3-(4-Methoxyphenyl)-2-oxo-1-phenyl(1,3,4-trihydropyrimidino[4,5-d]pyrimidin-7-yl)]-N-phenylbutanamide.

6. The compound of claim 2 which is selected from the group:
N-(4-Hydroxyphenyl)-N-[3-(4-methoxyphenyl)-2-oxo-1-phenyl(1,3,4-trihydropyrimidino[4,5-d]pyrimidin-7-yl)]acetamide; and
N-(4-Hydroxyphenyl)-N-[3-(4-methoxyphenyl)-2-oxo-1-phenyl(1,3,4-trihydropyrimidino[4,5-d]pyrimidin-7-yl)]acetamide.

7. The compound of claim 1 wherein R¹ is —COOCHR⁵OCOR⁴.

8. The compound of claim 7 wherein R² is H.

9. The compound of claim 8 wherein R³ is H.

10. The compound of claim 9 which is selected from the group:
{N-[3-(4-Methoxyphenyl)-2-oxo-1-phenyl(1,3,4-trihydropyrimidino[4,5-d]pyrimidin-7-yl)]-N-phenylcarbamoyloxy}methyl acetate;

{N-[3-(4-Methoxyphenyl)-2-oxo-1-phenyl(1,3,4-trihydropyrimidino[4,5-d]pyrimidin-7-yl)]-N-phenylcarbamoyloxy}methyl 2-(dimethylamino)acetate;

{N-[3-(4-Methoxyphenyl)-2-oxo-1-phenyl(1,3,4-trihydropyrimidino[4,5-d]pyrimidin-7-yl)]-N-phenylcarbamoyloxy}methyl 2-(dimethylamino)acetate hydrochloric acid salt; and {N-[3-(4-Methoxyphenyl)-2-oxo-1-phenyl(1,3,4-trihydropyrimidino[4,5-d]pyrimidin-7-yl)]-N-phenylcarbamoyloxy}methyl piperidine-4-carboxylate trifluoroacetic acid salt.

11. The compound of claim 1 wherein $R^1$ is H.

12. The compound of claim 11 wherein $R^2$ is H.

13. The compound of claim 12 which is selected from the group:

3-(4-Methoxyphenyl)-1-phenyl-7-(phenylamino)-1,3,4-trihydropyrimidino[4,5-d]pyrimidin-2-one;

3-(4-Methoxyphenyl)-1-phenyl-7-(phenylamino)-1,3,4-trihydropyrimidino[4,5-d]pyrimidin-2-one methanesulfonate salt;

7-[(4-Hydroxyphenyl)amino]-3-(4-methoxyphenyl)-1-phenyl-1,3,4-trihydropyrimidino[4,5-d]pyrimidin-2-one; and 3-(4-Methoxyphenyl)-7-[(4-methoxyphenyl)amino]-1-phenyl-1,3,4-trihydropyrimidino[4,5-d]pyrimidin-2-one.

14. A compound selected from the group:

3-(4-Methoxyphenyl)-1-phenyl-7-(phenylamino)-1,3,4-trihydropyrimidino[4,5-d]pyrimidin-2-one, 3-(4-Methoxyphenyl)-1-phenyl-7-(phenylamino)-1,3,4-trihydropyrimidino[4,5-d]pyrimidin-2-one methanesulfonate salt, 7-[(4-Hydroxyphenyl)amino]-3-(4-methoxyphenyl)-1-phenyl-1,3,4-trihydropyrimidino[4,5-d]pyrimidin-2-one, and 3-(4-Methoxyphenyl)-7-[(4-methoxyphenyl)amino]-1-phenyl-1,3,4-trihydropyrimidino[4,5-d]pyrimidin-2-one.

15. A compound selected from the group:

(Chloromethoxy)-N-[3-(4-methoxyphenyl)-2-oxo-1-phenyl(1,3,4-trihydropyrimidino[4,5-d]pyrimidin-7-yl)]-N-benzamide 3-(4-Methoxyphenyl)-1-phenyl-7-{[4-(1,1,2,2-tetramethyl-1-silapropoxy) phenyl]amino}-1,3,4-trihydropyrimidino[4,5-d]pyrimidin-2-one, and N-[3-(4-Methoxyphenyl)-2-oxo-1-phenyl(1,3,4-trihydropyrimidino[4,5-d]pyrimidin-7-yl)]-N-[4-(1,1,2,2-tetramethyl-1-silapropoxy)phenyl]acetamide.

16. A method of- treating lung, colon or prostate cancer, comprising administering to a patient in need of such treatment a therapeutically effective amount of a compound of claim 1.

17. A compound selected from the group:

(Chloromethoxy)-N-[3-(4-methoxyphenyl)-2-oxo-1-phenyl(1,3,4- trihydropyrimidino[4,5-d]pyrimidin-7-yl)]-N-benzamide, 3-(4-Methoxyphenyl)-1-phenyl-7-{[4-(1,1,2,2,=tetramethyl-1-silapropoxy)phenyl]amino{1,3,4-trihydropyrimidino[4,5-d]pyrimidin-2-one, and N-[3-(4-Mthoxyphenyl)-2-oxo-1-phenyl(1,3,4-trihydropyrimidino[4,5-d]pyrimidin-7-yl]- N-[4-(1,1,2,2,-tetramethyl-1-silapropoxy)phenyl]acetamide.

* * * * *

UNITED STATES PATENT AND TRADEMARK OFFICE
CERTIFICATE OF CORRECTION

PATENT NO. : 7,084,270 B2
APPLICATION NO. : 10/623972
DATED : August 1, 2006
INVENTOR(S) : Chen et al.

It is certified that error appears in the above-identified patent and that said Letters Patent is hereby corrected as shown below:

TITLE PAGE: item (73),
The Assignee information reads: "Hoffman-La Roche Inc., Nutley, NJ (US)". The Assignee information should read --Hoffmann-La Roche Inc., Nutley, NJ (US)--.

Claim 5, Column 39, line 59: "trihydropyrimidino [4,5-d]pyrimid-7-yl)]-N-" should read --trihydropyrimidino [4,5-d] pyrimidin-7-yl)]-N- --.

Claim 5, Column 39, line 63: "trihydropyrimidino [4,5-d] pyrimid-7-yl)]-N-" should read --trihydropyrimidino [4,5-d] pyrimidin-7-yl)]-N- --.

Claim 6, Column 40, line 56: "N-(4-Hydroxyphenyl)" should read -- N-(4-methoxyphenyl) --.

Signed and Sealed this

Ninth Day of January, 2007

JON W. DUDAS
*Director of the United States Patent and Trademark Office*